United States Patent
Fueyo et al.

(10) Patent No.: US 9,483,613 B2
(45) Date of Patent: *Nov. 1, 2016

(54) DETERMINATION OF NEUROPSYCHIATRIC THERAPY MECHANISMS OF ACTION

(71) Applicant: International Business Machines Corporation, Armonk, NY (US)

(72) Inventors: Joanna L. Fueyo, Sandwich, MA (US); Robert L. Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,987

(22) Filed: Sep. 16, 2015

(65) Prior Publication Data
US 2016/0004821 A1    Jan. 7, 2016

Related U.S. Application Data

(63) Continuation of application No. 12/169,350, filed on Jul. 8, 2008, now Pat. No. 9,198,612.

(51) Int. Cl.
*A61B 5/05* (2006.01)
*G06F 19/00* (2011.01)
(Continued)

(52) U.S. Cl.
CPC ............. *G06F 19/321* (2013.01); *A61B 5/055* (2013.01); *A61B 5/411* (2013.01); *A61B 5/417* (2013.01);
(Continued)

(58) Field of Classification Search
USPC ........................................................ 600/407
See application file for complete search history.

(56) References Cited

U.S. PATENT DOCUMENTS

| 5,832,450 A | 11/1998 | Myers et al. |
| 5,845,255 A | 12/1998 | Mayaud |

(Continued)

FOREIGN PATENT DOCUMENTS

| JP | 2005237441 A | 9/2005 |
| JP | 2006204641 A | 8/2006 |

(Continued)

OTHER PUBLICATIONS

European Search Report, dated Mar. 27, 2009, regarding Application No. EP08167756.9, 10 pages.
(Continued)

*Primary Examiner* — Joel F Brutus
(74) *Attorney, Agent, or Firm* — Yee & Associates, P.C.; Maeve Carpenter

(57) ABSTRACT

A computer implemented method, apparatus, and computer program product of determining mechanisms of action for therapies. A first set of brain scans for each subject in a plurality of subjects generated at a first time period and a second set of brain scans for each subject generated at a second time period are received. Each subject is diagnosed with a given condition and received a given therapy. A set of changes in the set of brain scans is identified for the each subject based on a comparison of a first set of regions of interest in the first set of scans for each subject with a second set of regions of interest in the second set of scans for each subject. A set of typical changes attributable to the given therapy is identified. A mechanism of action for the given therapy is generated based on the set of typical changes.

22 Claims, 9 Drawing Sheets

(51) Int. Cl.
*A61B 5/055* (2006.01)
*A61B 5/00* (2006.01)
*A61B 6/03* (2006.01)
*A61B 6/00* (2006.01)
*G06F 17/30* (2006.01)
*G06K 9/46* (2006.01)
*G06K 9/62* (2006.01)
*G06T 7/00* (2006.01)

(52) U.S. Cl.
CPC .............. *A61B 6/037* (2013.01); *A61B 6/501* (2013.01); *A61B 6/56* (2013.01); *A61B 6/563* (2013.01); *A61B 6/566* (2013.01); *G06F 17/30011* (2013.01); *G06F 17/30864* (2013.01); *G06F 19/345* (2013.01); *G06F 19/3443* (2013.01); *G06F 19/3481* (2013.01); *G06K 9/46* (2013.01); *G06K 9/6215* (2013.01); *G06T 7/0012* (2013.01); *G06F 19/324* (2013.01); *G06K 2009/4666* (2013.01); *G06T 2207/10088* (2013.01); *G06T 2207/10104* (2013.01); *G06T 2207/30016* (2013.01)

(56) References Cited

U.S. PATENT DOCUMENTS

| | | | |
|---|---|---|---|
| 5,873,823 | A | 2/1999 | Eidelberg et al. |
| 7,051,022 | B1 | 5/2006 | Faisal |
| 7,244,231 | B2 | 7/2007 | Dewing et al. |
| 7,269,516 | B2 | 9/2007 | Brunner et al. |
| 7,428,323 | B2 | 9/2008 | Hillman |
| 7,599,995 | B1 | 10/2009 | Fernandez et al. |
| 7,844,560 | B2 | 11/2010 | Krishnan et al. |
| 7,912,528 | B2 | 3/2011 | Krishnan et al. |
| 7,929,737 | B2 | 4/2011 | Sirohey et al. |
| 7,996,242 | B2 | 8/2011 | Fueyo et al. |
| 8,064,986 | B2 | 11/2011 | Profio et al. |
| 8,126,112 | B2 | 2/2012 | Massie et al. |
| 8,126,228 | B2 | 2/2012 | Fueyo et al. |
| 8,199,982 | B2 | 6/2012 | Fueyo et al. |
| 8,280,482 | B2 | 10/2012 | Rusinek et al. |
| 8,388,529 | B2 | 3/2013 | Fueyo et al. |
| 8,548,823 | B2 | 10/2013 | Fueyo et al. |
| 2003/0032069 | A1 | 2/2003 | Muraca |
| 2003/0100998 | A2 | 5/2003 | Brunner et al. |
| 2004/0093331 | A1 | 5/2004 | Garner et al. |
| 2005/0020903 | A1 | 1/2005 | Krishnan et al. |
| 2005/0038678 | A1 | 2/2005 | Qian et al. |
| 2005/0043965 | A1 | 2/2005 | Heller et al. |
| 2005/0091191 | A1 | 4/2005 | Miller et al. |
| 2005/0107682 | A1 | 5/2005 | Rao et al. |
| 2005/0215889 | A1 | 9/2005 | Patterson |
| 2005/0244036 | A1 | 11/2005 | Rusinek et al. |
| 2006/0120584 | A1 | 6/2006 | Hillman |
| 2006/0270926 | A1 | 11/2006 | Hu et al. |
| 2007/0129627 | A1 | 6/2007 | Profio et al. |
| 2007/0260488 | A1 | 11/2007 | Heywang-Kobrunner et al. |
| 2007/0276777 | A1 | 11/2007 | Krishnan et al. |
| 2008/0077001 | A1 | 3/2008 | Ruscio et al. |
| 2009/0006061 | A1 | 1/2009 | Thukral et al. |
| 2009/0124882 | A1 | 5/2009 | Massie et al. |
| 2009/0149898 | A1 | 6/2009 | Hulvershorn et al. |
| 2009/0316968 | A1 | 12/2009 | Fueyo et al. |
| 2009/0316969 | A1 | 12/2009 | Fueyo et al. |
| 2010/0010316 | A1 | 1/2010 | Fueyo et al. |
| 2010/0010363 | A1 | 1/2010 | Fueyo et al. |
| 2010/0010827 | A1 | 1/2010 | Fueyo et al. |
| 2010/0010831 | A1 | 1/2010 | Fueyo et al. |
| 2012/0207362 | A1 | 8/2012 | Fueyo et al. |

FOREIGN PATENT DOCUMENTS

| | | |
|---|---|---|
| WO | WO2007019504 A2 | 2/2007 |
| WO | WO2007063656 A1 | 6/2007 |

OTHER PUBLICATIONS

Japanese Patent Office Notification of Reasons for Rejection, dated Aug. 11, 2009, regarding Application No. JP2008-279718, 4 pages.

Aberle et al, Database Design and Implementation for Quantitative Image Analysis Research, IEEE Transactions on Information Technology in Biomedicine, vol. 9, No. 1, Mar. 2005, pp. 99-108.

Barrett et al, "Regional CBF in chronic stable TBI treated with hyperbaric oxygen," Undersea & Hyperbaric Medicine; vol. 31, No. 4, Winter 2004, pp. 395-406.

Rahman et al, "Medical Image Retrieval and Registration: Towards Computer Assisted Diagnostic Approach," Proceedings of the IDEAS Workshop on Medical Information Systems: The Digital Hospital (IDEAS-DH'04), Sep. 2004, pp. 78-89.

Office Action, dated Sep. 22, 2011, regarding U.S. Appl. No. 12/141,316, 28 pages.

Notice of Allowance, dated Feb. 9, 2012, regarding U.S. Appl. No. 12/141,316, 7 pages.

Office Action, dated Nov. 27, 2009, regarding U.S. Appl. No. 12/169,339, 28 pages.

Final Office Action, dated Apr. 12, 2010, regarding U.S. Appl. No. 12/169,339, 17 pages.

Notice of Allowance, dated Nov. 2, 2012, regarding U.S. Appl. No. 12/169,339, 9 pages.

Office Action, dated Oct. 28, 2010, regarding U.S. Appl. No. 12/169,402, 27 pages.

Notice of Allowance, dated Apr. 6, 2011, regarding U.S. Appl. No. 12/169,402, 14 pages.

Office Action, dated Jul. 7, 2011, regarding U.S. Appl. No. 12/141,322, 15 pages.

Office Action, dated Jul. 7, 2011, regarding U.S. Appl. No. 12/169,329, 24 pages.

Final Office Action, dated Jan. 26, 2012, regarding U.S. Appl. No. 12/169,329, 19 pages.

Notice of Allowance, dated Feb. 22, 2013, regarding U.S. Appl. No. 12/169,329, 15 pages.

Notice of Allowance, dated May 24, 2013, regarding U.S. Appl. No. 12/169,329, 9 pages.

Office Action, dated Jan. 20, 2012, regarding U.S. Appl. No. 12/169,350, 28 pages.

Office Action, dated Jul. 17, 2012, regarding U.S. Appl. No. 12/169,350, 34 pages.

Final Office Action, dated Feb. 8, 2013, regarding U.S. Appl. No. 12/169,350, 34 pages.

Office Action, dated Jun. 11, 2014, regarding U.S. Appl. No. 12/169,350, 37 pages.

Final Office Action, dated Jul. 31, 2014, regarding U.S. Appl. No. 12/169,350, 26 pages.

Office Action, dated Oct. 8, 2014, regarding U.S. Appl. No. 12/169,350, 24 pages.

Office Action, dated Feb. 4, 2015, regarding U.S. Appl. No. 12/169,350, 9 pages.

Office Action, dated Apr. 16, 2015, regarding U.S. Appl. No. 12/169,350, 6 pages.

Notice of Allowance, dated Jul. 27, 2015, regarding U.S. Appl. No. 12/169,350, 10 pages.

Office Action, dated Feb. 2, 2016, regarding U.S. Appl. No. 13/452,331, 53 pages.

Notice of Allowance, dated Apr. 8, 2016, regarding U.S. Appl. No. 13/452,331, 13 pages.

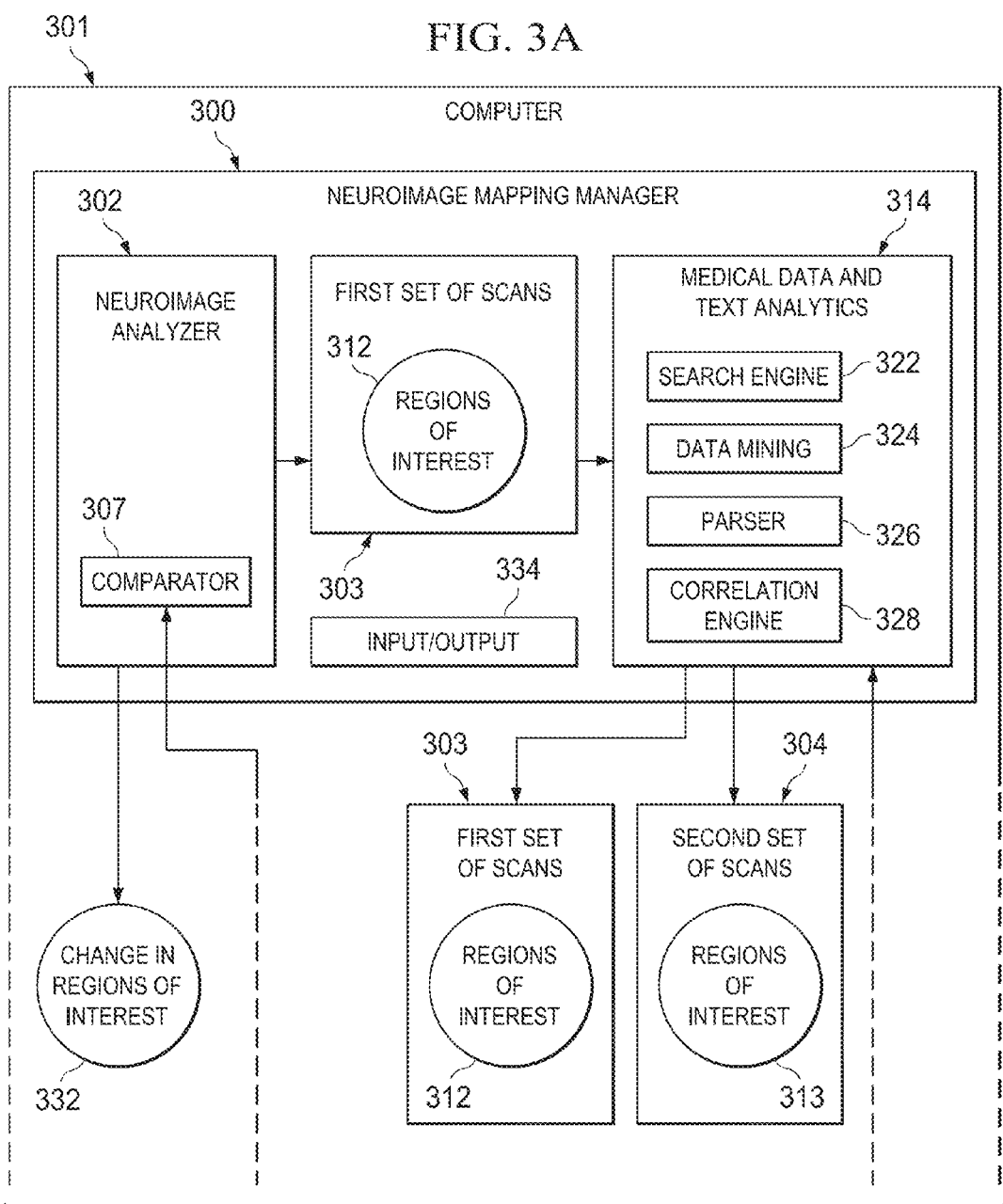

DETERMINATION OF NEUROPSYCHIATRIC THERAPY MECHANISMS OF ACTION

This application is a continuation of prior application Ser. No. 12/169,350, filed Jul. 8, 2008.

BACKGROUND OF THE INVENTION

1. Field of the Invention

The present invention is related generally to a data processing system and in particular to a method and apparatus for determining a mechanism of action of therapy. More particularly, the present invention is directed to a computer implemented method, apparatus, and computer usable program code for automatically determining the mechanism of action for neuropsychiatric therapies via automation of the assessment of neuroimage data and medical literature.

2. Description of the Related Art

Neuropsychiatric conditions typically have neurological features associated with disorders of the nervous system, as well as psychiatric features. Neuropsychiatric conditions may be treated using a variety of therapies, such as talk therapy, behavioral therapy, chemical therapy, and/or mechanical therapy. Chemical therapy refers to pharmacotherapy, such as, the utilization of drugs. Mechanical therapy includes electroconvulsive therapies (ECT) and deep brain stimulation (DBS). These therapies may be used separately or may be used in combination to treat patients. However, some patients may not receive the most effective treatments available due to difficulties in accurately diagnosing patients with neuropsychiatric conditions and determining accurate mechanisms of action in drug therapies. The determination of mechanisms of action in drugs may be a time consuming, tedious, and expensive process, particularly in complex cases.

BRIEF SUMMARY OF THE INVENTION

According to one embodiment of the present invention, a computer implemented method, apparatus, and computer program product for determining mechanisms of action for therapies is provided. The process receives a plurality of brain scans for a plurality of subjects. The plurality of brains scans comprises a first set of brain scans for each subject in the plurality of subjects generated at a first time period and a second set of brain scans for each subject in the plurality of subjects generated at a second time period. Each subject in the plurality of subjects is diagnosed with a given condition and each subject is receiving a given therapy. The given therapy may be a pharmacotherapy, a mechanical therapy, or talk therapy.

A set of electronic medical literature sources is automatically searched for portions of medical literature describing the given therapy. A first set of regions of interest in the first set of brain scans for each subject and a second set of regions of interest in the second set of brain scans are automatically identified for each subject. A set of changes in the set of brain scans is identified for each subject based on a comparison of the first set of regions of interest for each subject with the second set of regions of interest for each subject. The set of changes comprises indicators of change occurring after each subject begins receiving the given therapy. The set of changes for each subject is analyzed with the portions of the medical literature describing the given therapy to identify a set of typical changes attributable to the given therapy. A mechanism of action for the given therapy is generated based on the set of typical changes.

In another embodiment, the plurality of subjects comprises subjects from various demographic groups. Each subject in the plurality of subjects receives the given therapy after the first set of scans were taken at the first time and before the second set of scans were taken at the second time. Additional subject data for each subject may also optionally be analyzed with the set of typical changes and portions of the medical literature associated with the given therapy to generate the mechanism of action. The additional subject data may include clinical data, subject medical history, subject data, and/or cognitive data.

In one embodiment, the portions of the medical literature may include medical literature relevant to the given condition, the given therapy, and the set of changes occurring over time to form the portions of the medical literature. The portions of the medical literature are analyzed with the set of typical changes occurring over time to derive the mechanism of action for the given therapy. The mechanism of action comprises a set of links to the portions of the medical literature associated with the given therapy and each change in the set of typical changes.

In yet another embodiment, a set of brain scans for a set of healthy subjects in various demographic groups is received to form the baseline normal scans. The baseline normal scans are analyzed to identify a normal appearance of areas in normal brain scans, wherein a normal brain scan is a scan that does not show indications of disease or abnormalities in the areas in the normal brain scans. The set of changes for each subject is compared with the baseline normal scans to identify the drug mechanism of action.

In another embodiment, other therapies being applied to a given subject in the plurality of subjects and/or other medical conditions in the plurality of subjects are identified. Changes in the set of scans for the given subject that are attributable to the other therapies and/or the other medical conditions are identified as uncorrelated changes. The uncorrelated changes are removed from the set of typical changes.

BRIEF DESCRIPTION OF THE SEVERAL VIEWS OF THE DRAWINGS

FIGS. 3A and 3B is a block diagram of a neuroimage mapping manager and a therapy mechanism generator in accordance with an illustrative embodiment;

DETAILED DESCRIPTION OF THE INVENTION

Figure 1:
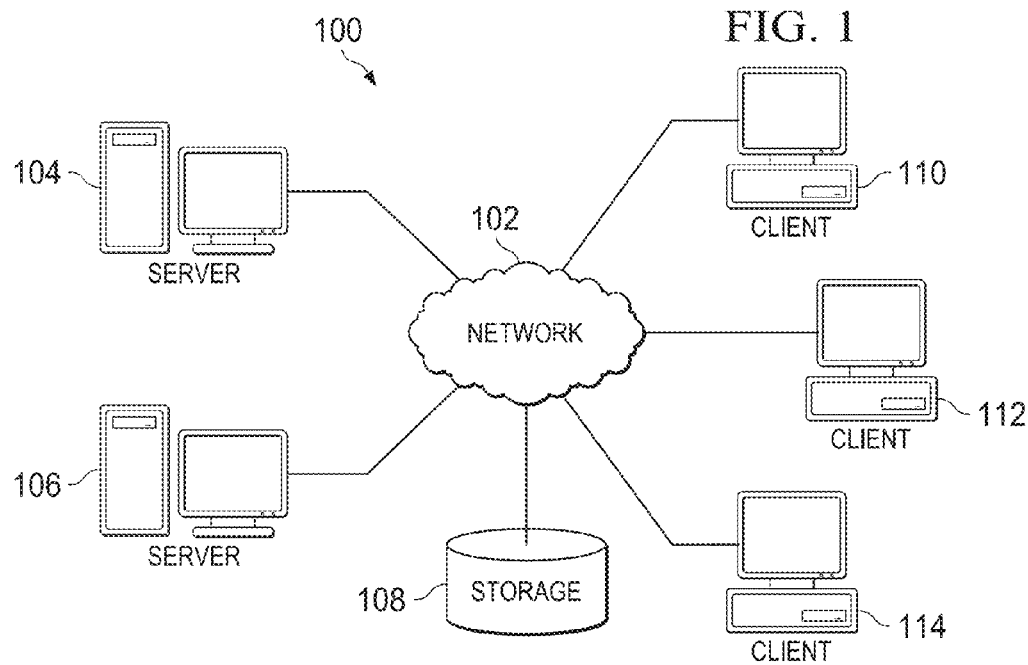
FIG. 1 is a pictorial representation of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

Figure 2:
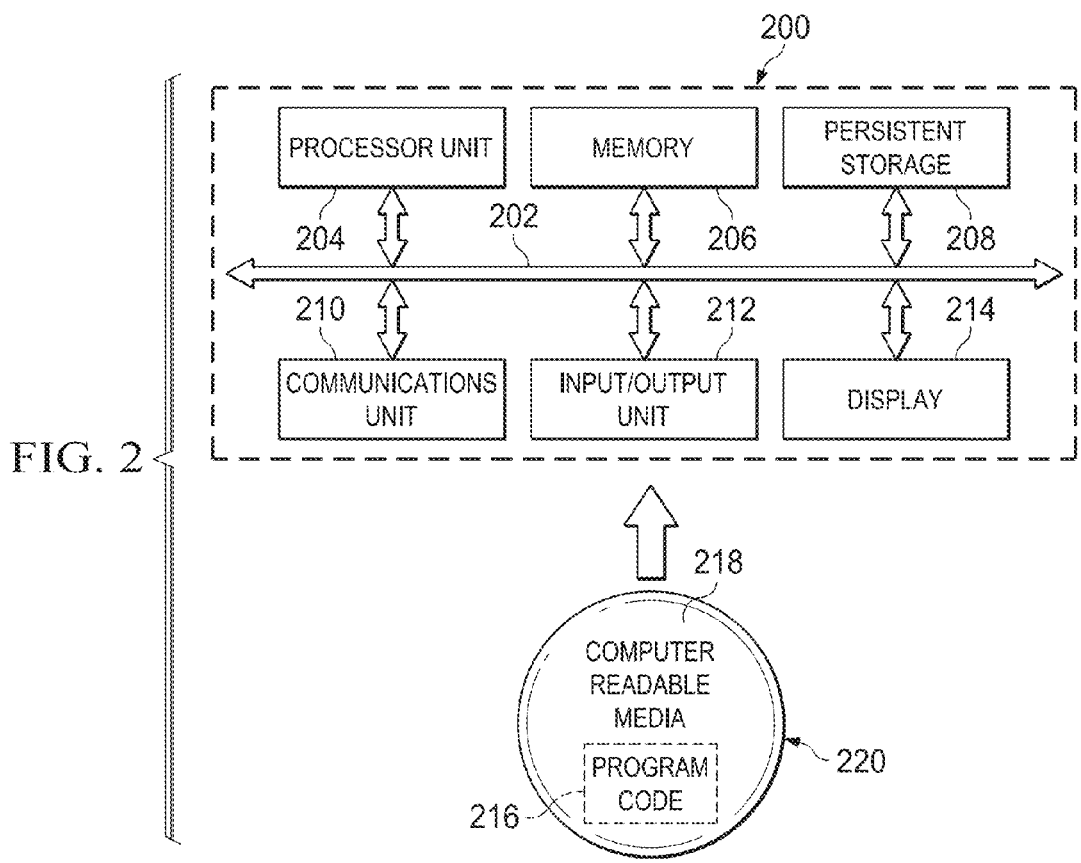
FIG. 2 is a block diagram of a data processing system in which illustrative embodiments may be implemented.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communication links or wireless transmissions containing the program code.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments recognize that patients may suffer from the negative side effects of effective therapies and/or trails of ineffective therapies due to a lack of detailed information describing mechanisms of action. Furthermore, the mechanism of action for a given therapy may be altered or modified due to drug interactions and utilization of other therapies in conjunction with the given therapy. In such cases, it may be difficult or impossible to clearly delineate a mechanism of action for the multiple therapies utilized in these complex cases.

Therefore, one embodiment provides a computer implemented method, apparatus, and computer program product for determining mechanisms of action for therapies. The process receives a plurality of brain scans for a plurality of subjects. The subjects may be patients, volunteers, participants in a drug study, paid participants, or any other human subjects. The plurality of brains scans comprises a first set of brain scans for each subject in the plurality of subjects generated at a first time period and a second set of brain scans for each subject in the plurality of subjects generated at a second time period. As used herein, the term "set" refers to one or more, unless indicated otherwise. Thus, the first set of brain scans is a set of one or more brain scans. A brain scan may be a positron emission tomography (PET) scan, a magnetic resonance imaging (MRI) scan, an x-ray scan, or any other type of brain scan.

Each subject in the plurality of subjects is diagnosed with a given condition and each subject is receiving a given therapy. The given therapy may be a pharmacotherapy, a mechanical therapy, or talk therapy. The given condition in this embodiment is a neuropsychiatric condition.

A set of electronic medical literature sources is automatically searched for portions of medical literature describing the given therapy. A first set of regions of interest in the first set of brain scans for each subject and a second set of regions of interest in the second set of brain scans are automatically identified for each subject. A region of interest is an area in a brain scan that includes a set of indicators associated with the mechanism of action of the given therapy. An indicator is a structural feature, level of brain chemistry, indicator of brain metabolism, indicator of active regions and/or inactive regions of the brain, and other features shown in a brain scan.

A set of changes in the set of brain scans is identified for each subject based on a comparison of the first set of regions of interest for each subject with the second set of regions of interest for each subject. The set of changes includes indicators of change occurring after each subject begins receiving the given therapy. An indicator is any feature or characteristic of an area in a scan. The set of changes for each subject is analyzed with the portions of the medical literature describing the given therapy to identify a set of typical changes attributable to the given therapy. A mechanism of action for the given therapy is generated based on the set of typical changes.

Figure 3B:
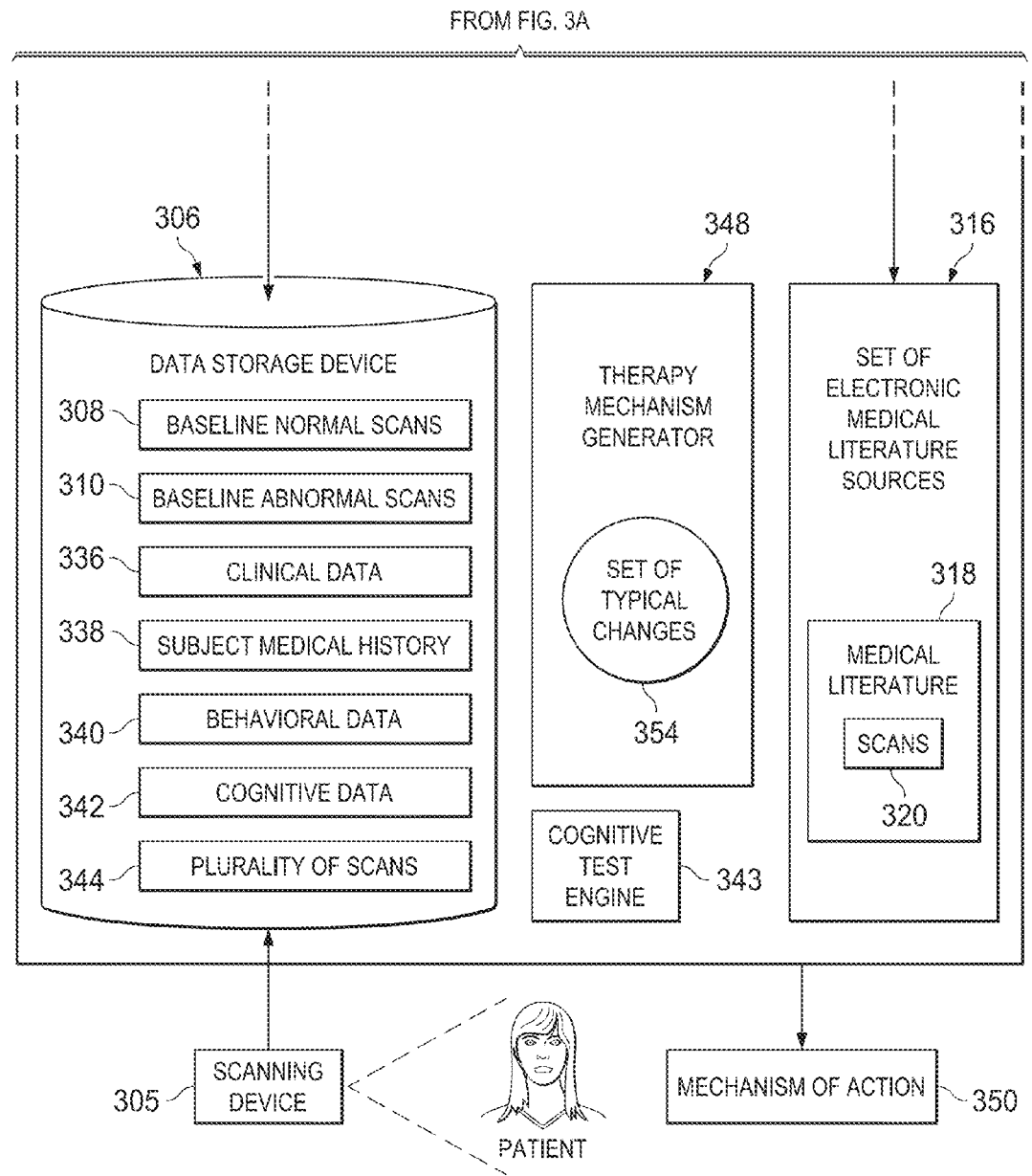

FIGS. 3A and 3B is a block diagram of a neuroimage mapping manager in accordance with an illustrative embodiment. Neuroimage mapping manager 300 is software for analyzing subject brain scans to identify regions of interest in the brain scans and generate links to portions of interest in the medical literature. Computer 301 may be implemented in any type of computing device, such as, without limitation, a server, a client, a laptop computer, a personal digital assistant (PDA), a smart phone, or any other known or available computing device shown in FIG. 1 and FIG. 2.

Neuroimage analyzer 302 receives first set of scans 303. First set of scans 303 is a set of one or more scans of a subject's brain generated at a first time. The first time may be a time prior to beginning implementation of one or more therapies or a given time after beginning one or more therapies. Second set of scans 304 is a set of scans of the subject generated at a second time. The second time is a given period of time after the first time. The second time may be, for example and without limitation, a day, a week, a month, six months, a year, two years, or any other time period after the first time. The second time is a given amount of time after beginning implementation of one or more therapies in a treatment plan to treat a subject.

First set of scans 303 and second set of scans 304 may include functional magnetic resonance imaging (fMRI) scans, structural magnetic resonance imaging (sMRI) scans, positron emission tomography (PET) scans, and/or any other type of brain scans. In other words, first set of scans 303 may include only positron emission tomography scans, only magnetic resonance imaging scans, or a combination of positron emission tomography scans and magnetic resonance imaging scans. The scans in first set of scans 303 may be generated by one or more scanning devices, such as scanning device 305.

Scanning device 305 may be implemented as one or more of a functional magnetic resonance imaging device, a structural magnetic resonance imaging device, a positron emission tomography device, or any other type of device for generating scans of a human subject's brain. As used herein, the term "subject" is not limited to a patient admitted in a hospital. The term "subject" may refer to any person obtaining medical care, consulting a medical practitioner, participating in a medical study, obtaining medical advice, or otherwise participating in medical tests and/or medical procedures.

Scanning device 305 in this example is a single scanning device. However, scanning device 305 may also include two or more scanning devices. Scanning device 305 optionally saves the scans of the subject's brain in data storage device 306. Data storage device 306 may be implemented as a hard drive, a flash memory, a main memory, read only memory (ROM), a random access memory (RAM), or any other type of data storage device. Data storage may be implemented in a single data storage device or a plurality of data storage devices. Thus, neuroimage analyzer 302 may receive the scans in first set of scans 304 from scanning device 305 as each scan is generated, or neuroimage analyzer 302 may retrieve the scans from a pre-generated set of scans stored in data storage device 306.

Comparator 307 is a software component that compares first set of scans 304 to baseline normal scans 308 and/or baseline abnormal scans 310 to identify regions of interest 312 first set of scans 303 and regions of interest 313 in second set of scans. A region of interest is an area in a scan that shows an indication of a potential abnormality, a potential illness, a potential disease, a potential condition, or any other deviation from what would be expected in a scan of the region for a healthy individual having similar characteristics as the subject. The similar characteristics may include, without limitation, an age range of the subject, gender, pre-existing conditions, or other factors influencing the development, function, structure, and appearance of an area of the brain as shown in a scan.

Baseline normal scans 308 may include, without limitation, a set of one or more brain scans for average, healthy subjects having one or more characteristics in common with the subject. The characteristics in common may be age, gender, pre-existing conditions, profession, place of residence, nationality, or any other characteristic. For example, if the subject is a sixteen year old female, baseline normal scans 308 may include scans of normal, healthy female subjects between the ages of fourteen and eighteen. Comparator 307 compares one or more areas in each scan in first set of scans 303 with corresponding areas in one or more scans in baseline normal scans 308 to identify areas of the subject's scans that are consistent with the scans of normal, healthy subjects and to identify areas of the scans that are inconsistent with the scans of normal, healthy subjects. An area in a scan that is inconsistent with the corresponding areas in baseline normal scans 308 are identified as a region of interest in regions of interest 312. A region identified in regions of interest 312 and 313 may indicate a potential abnormality, illness, or condition. However, each region in regions of interest 312 and/or 313 are not required to definitively indicate an abnormality, illness, condition, or other deviation from the norm.

Baseline abnormal scans 310 is a set of one or more scans of subjects having one or more characteristics in common with the subject and diagnosed with an identified condition. The identified condition may be a disease, an illness, a deformity, an abnormality, or any other identified deviation from the norm. For example, if the subject is a male, age thirty five, and diagnosed with diabetes, the baseline abnormal scans may include scans of male subjects between the ages of thirty and forty and having a variety of known neuropsychiatric disorders. Comparator 307 compares regions in each scan in first set of scans 303 with one or more scans in baseline abnormal scans 310 to identify regions of interest in the subject's scans that show indications of disorders, illness, disease, or abnormalities. A region in a scan may show indications of a potential illness, condition, abnormality, or neuropsychiatric disorder if the region in the subject's scan is consistent with a corresponding region in a brain scan of a subject having a known illness, condition, abnormality, or neuropsychiatric disorder. Thus, neuroimage analyzer 302 analyzes first set of scans 303 to identify regions of interest in the scans based on baseline normal scans and/or baseline disorder scans for identified illnesses, abnormalities, diseases, disorders, or other known conditions.

Medical data and text analytics 314 is a software component for searching set of electronic medical literature sources 316 for medical literature relevant to regions of interest 312 in first set of scans 304. Set of electronic medical literature sources 316 is a set of one or more sources of medical literature 318. Set of electronic medical literature sources 316 may include both online medical literature sources that are accessed by medical data and text analytics 314 via a network connection, as well as off-line medical literature sources that may be accessed without a network connection. An example of an electronic medical literature source includes, without limitation, PUBMED. Medical literature 318 is any literature, journal article, medical study results, medical text, pharmaceutical studies, or any other medical information in an electronic format. Medical literature 318 may include scans 320, such as magnetic resonance imaging scans, positron emission tomography scans, or any other type of brain scans.

Medical data and text analytics 314 comprises search engine 322. Search engine 322 is any type of known or available information retrieval software for locating medical literature that is relevant to regions of interest 312 in set of electronic medical literature sources 316. Search engine 322 may be software for searching data storage devices on a computer system or a web search tool for searching for medical information on the World Wide Web. Search engine 322 may also make queries into databases, information systems, and other medical literature information sources to locate information relevant to regions of interest 312.

Data mining 324 is a software tool for searching through information available from one or more sources and retrieving medical information relevant to regions of interest 312. Data mining 324, search engine 322, or any other software for locating relevant information may be used to search set of electronic medical literature sources 316 for relevant medical literature. Searching through the information from one or more sources may include, without limitation, using at least one of data mining, search engines, pattern recognition, queries to identify the relevant medical literature in the medical literature available from the set of electronic medical literature sources, data mining cohort, pattern recognition cohort, search engine cohort, or any other cohort appliance of interest. The term "at least one" refers to one or more and in any combination. Thus, the searching may include data mining only, data mining and pattern recognition, search engines, pattern recognition, and queries, or any other combination.

A cohort is a group of one or more objects having a common characteristic. For example, a data mining cohort may be, without limitation, a group of one or more objects associated with performing data mining techniques to identify desired data from a data source. A pattern recognition cohort may be, without limitation, a group of pattern recognition software applications that identify patterns in data, such as medical data.

Parser 326 is software for parsing medical literature 318 text into a form suitable for further analysis and processing. Parser 326 may be implemented as any type of known or available parser. Correlation engine 328 correlates portions of medical literature 318 with regions of interest 312 to form portions of medical literature 318 that are relevant or associated with regions of interest 312. A portion of medical literature is a section of medical literature text and/or one or more scans that describes a region of interest, describes a condition, illness, deformity, abnormality, disease, or other cause for an appearance of a region of interest, an area in a scan that is the same or similar to an area of interest, an area in a scan in scans 320 or a portion of text in a medical literature document that is otherwise associated with a characteristic, feature, structure, indicator of brain chemistry, indicator of brain function, or other feature shown in an area of interest in a subject's brain scan.

For example, if a region of interest in subject's brain scan indicates an enlargement of a brain ventricle, a scan in scans 320 in medical literature 318 showing a similar enlargement of the brain ventricle is a portion of medical literature that is relevant or associated with regions of interest 312. Likewise, if a section of a medical journal article in an electronic format in medical literature 318 describes various causes of enlargement of a brain ventricle, that section of the medical literature is also relevant or associated with regions of interest 312. Thus, in this example, portions of medical literature 318 include both the scan showing the enlargement of the ventricle in a different subject and the portion of the medical journal article discussing possible causes of an enlargement of the ventricles in subjects.

In this manner, medical data and text analytics 314 is capable of automatically searching for electronic medical literature, identifying portions of the medical literature that are relevant to a particular subject's diagnosis and/or treatment, and correlate each item, such as a scan or a section in a journal article, to each region of interest in the subject's brain scans. When a user wishes to view all the relevant medical literature associated with a particular region of interest, the user can simply request all the portions of medical literature correlated to the particular region of interest. In response, neuroimage mapping manager 300 only provides the portions of medical literature 318 from a plurality of medical literature sources that may be useful to the user, rather than providing the full text of all medical journal articles that have certain key words or search phrases, as is currently done.

Neuroimage mapping manager 300 may also generate a set of links to portions of medical literature 318 describing or associated with regions of interest 312 and/or regions of interest 313. Regions of interest 312 and/or 313 may also optionally include an identification of a source and/or citation for the source of each portion of medical literature linked to the regions of interest. The set of links to portions of medical literature 318 may be embedded in first set of scans 303 and/or second set of scans 304, or embedded within regions of interest 312 in first set of scans 303 and/or regions of interest 313 in second set of scans 304. The set of links to portions of medical literature 318 may also optionally be presented as a separate result apart from first set of scans 304 and/or apart from regions of interest 312. In another embodiment, the set of links to portions of medical literature 318 are embedded in an electronic medical file for the subject or a file for brain scan results for one or more subjects. A user selects a link in the set of links to view a portion of medical literature associated with a region of interest. In such a case, the portions of medical literature 318 in the subject's medical file may include a set of links to first set of scans 303 and second set of scans 304 and/or a set of links to regions of interest 312 and 313. In such a case, each portion of the medical literature, such as a scan or a section of a medical journal article, may include a link to the region of interest that is associated with or relevant to that portion of the medical literature. Likewise, all the portions of the medical literature that are relevant to a particular region of interest may include a single link to that particular region of interest rather than each portion of the medical literature including a separate link to the particular region of interest or regions of interest associated with the portions of the medical literature.

The portion of medical literature may be a scan only, text only, or a combination of text and one or more scans. The portion of medical literature may be an entire or complete item, such as a complete medical journal article or a complete section of a medical textbook, if the entire journal article or complete section of the medical text is relevant to the features shown in a particular region of interest. The portion of medical literature may also be a portion of a journal article, a portion of a section of a medical textbook, or other part of an item of medical literature. In such a case, a user may optionally select to view the entire journal article or the entire medical text rather than viewing only the relevant portion of the journal article or medical text.

In this embodiment, baseline normal scans 308 and baseline abnormal scans 310 are pre-generated and available for retrieval from data storage device 306. However, in another embodiment, medical data and text analytics 314 searches set of electronic medical literature sources 316 for scans of normal, healthy subjects to create baseline normal scans 308. Medical data and text analytics 316 also searches set of electronic medical literature sources 316 for scans of subjects having known abnormalities, deformities, illnesses, ailments, diseases, or other neuropsychiatric disorders to create baseline abnormal scans 310.

Thus, neuroimage mapping manager 300 provides data and text analytics to automatically determine regions of a subject's brain affected by neuropsychiatric conditions and/or other illness or abnormality as depicted in functional neuroimage data. Neuroimage data is data associated with a brain scan, such as functional magnetic resonance imaging and positron emission tomography scans. Neuroimage mapping manager 300 applies technologies to data, such as heuristics, which automatically correlate the features identified in regions of interest 312 with relevant portions of medical literature 318 that describes regions of interest 312.

Comparator 307 also compares regions of interest 312 in first set of scans 304 with regions of interest 314 in second set of scans 305 to identify one or more changes in the regions of interest 332 over time. Changes in regions of interest 332 is an identification of changes or differences in the regions of interest in first set of scans 303 and second set of scans 304. For example, if a comparison of first set of scans 303 with second set of scans 304 shows that brain metabolism in a first region of interest has increased and a disruption of activity has occurred in a second region, these changes are identified in changes in regions of interest 332. Change in regions of interest 332 may also include a set of links to portions of medical literature 318 associated with or describing the changes.

Input/output 334 may be implemented as any type of input and/or output device for presenting output to a user and receiving input from a user. For example, input/output 334 may present regions of interest 312 to a user and/or receive a selection of one or more regions of interest from a user. Input/output 334 may also be used to present set of diagnoses, treatment plans, or other information to a user. Neuroimage analyzer 302 may optionally present the automatically selected regions of interest to the user using input/output 334. The automatically selected regions of interest may be presented using a display device to present the regions of interest in a visual format, using an audio device to present the regions of interest to the user in an audio format, using a tactile interface that may be read by the visually impaired, using a combination of audio and visual devices, using a combination of audio and tactile devices, or any other presentation device.

The user may utilize input/output 334 to choose to select one or more additional regions of interest in first set of scans 303 and/or second set of scans 304. In such a case, neuroimage analyzer 302 adds the manually selected set of one or more regions of interest to regions of interest 312. In one embodiment, the regions of interest that are not automatically selected by neuroimage analyzer 302 and/or regions of interest that are not manually selected by the user are automatically removed by neuroimage analyzer 302. In another embodiment, the user may choose to manually de-select or remove one or more regions of interest that was automatically selected by neuroimage analyzer 302. In such a case, neuroimage analyzer 302 automatically removes the one or more regions of interest selected for removal by the user from regions of interest 312.

In another embodiment, neuroimage mapping manager 300 makes a determination as to whether indicators correlate with the subject's clinical data. Clinical data 336 is data describing the results of clinical laboratory tests. Clinical data 336 may include, without limitation, urinalysis tests, blood tests, thyroid tests, biopsy results, cultures, electrolyte tests, genetic tests, bone marrow tests, tests for the presence of viral agents/illness, tests for the presence of bacterial agents/illnesses, hormone tests, or any other type of laboratory tests. Clinical data 336 describes the presence of substances in the blood, urine, tissue, hormone levels, body chemistry, and body fluids. Clinical data 336 may be relevant to diagnosis or therapy for a particular condition.

Moreover, clinical data 336 may reveal causes of one or more features in the brain scans. For example, clinical tests may indicate mercury poisoning or other substances in the blood that may be responsible for the abnormal appearance of a region in a brain scan. Clinical data 336 for a particular subject may be available on data storage device 306, obtained from a remote data storage device via a network connection, and/or may be manually input to neuroimage mapping manager through input/output device 334. If the features in a region of interest correlate with clinical data 336, neuroimage mapping manager 300 identifies the correlations. The correlations may be provided as links to information embedded within regions of interest 312 and/or 313 or provided separately from the regions of interest.

Subject medical history 338 is a record of the subject's past and current medical treatments, prescribed drugs, medical procedures, diagnoses, treating physicians, known allergies, and/or any other medical information associated with the subject. Neuroimage mapping manager 300 may correlate information in subject medical history that may be responsible for an appearance or presence of a feature in a region of interest with that particular region in regions of interest 312.

For example, if subject medical history 338 indicates that the subject suffered a head trauma in a car accident when the subject was a child that led to structural damage in a particular area of the brain, that information is linked to the region of interest corresponding to the area of the brain where the head trauma occurred. Likewise, if the subject had brain surgery to prevent or lessen the effects of seizures and the epilepsy surgery effects brain function in one or more areas of the brain, the regions of interest that are correlated to the areas of the brain effected by the epilepsy surgery are identified in regions of interest 312 with a link to the portion of the subject medical history 338 discussing the epilepsy surgery and effects of the epilepsy surgery.

In another embodiment, neuroimage mapping manager 300 makes a determination as to whether change in regions of interest 332 correlate with the subject's clinical data or medical history. For example, clinical tests may indicate mercury poisoning or other substances in the blood that may be responsible for the changes in brain chemistry and/or brain function shown in the brain scans. If the changes in regions of interest 332 correlate with the clinical data or medical history, neuroimage mapping manager 300 identifies the correlations in change in regions of interest 332 or the correlations may be identified in a separate output provided separately from change in regions of interest over time 332.

Behavioral data 340 is metadata describing the appearance of the subject, the actions of the subject, events associated with the subject, and any other behavior related data. For example, and without limitation, behavioral data 340 may indicate that the subject is wearing multiple layers of clothing on a warm summer day. The behavioral data may describe behavioral tics, such as verbal tics, unprovoked use of profanity, locking and unlocking doors, turning lights on and off, lacing and unlacing shoes, or other repetitive behaviors.

Behavioral data 340 may also describe behaviors, such as, without limitation, pacing, a running monologue or talking with oneself, an appearance of confusion, or other actions. The behavioral data may also describe an appearance of a person's face and emotions apparent on the subject's face. For example, and without limitation, the behavioral data may describe an angry look, such as frowning and dilated pupils in conjunction with utilization of a loud voice and throwing objects to identify angry or hostile behavior. Behavioral data 340 may indicate that the subject sat in a single location, did not speak, did not react to other people or external stimuli, and had a fixed stare for a given period of time to indicate that the subject is unemotional, dissociated, or catatonic. Behavioral data 340 may be provided manually by a user or generated automatically by digital video analysis software, such as, without limitation, International Business Machines (IBM) smart surveillance system (S3).

Cognitive data 342 is data describing results of cognitive tests and psychological evaluations. Cognitive data 342 may include results of Rorschach ink blot tests, memory tests, intelligence quotient (IQ) tests, problem solving, language skills tests, perception tests, and other results of cognitive and psychological evaluations. Cognitive data 342 may be entered by a user manually using input/output 334. Cognitive data 342 may also be generated automatically by cognitive test engine 343. Cognitive test engine 343 is software for administering cognitive tests and psychological tests to a subject. Cognitive test engine 343 may use input/output 334 to present a set of cognitive and psychological test questions to the subject. The subject enters answers using input/output 334. The set of questions may be presented in an audio format, a video format, a tactile format, or a combination of audio, video, and/or tactile format. Cognitive test engine 343 analyzes the subject's responses to set of questions and generates cognitive data 342 based on the answers.

Plurality of scans 344 is a plurality of brain scans for a plurality of subjects. In other words, plurality of scans 344 includes brain scans of multiple different subjects taken at various time periods. Plurality of scans 344 includes a first set of brain scans for each subject in the plurality of subjects generated at a first time period and a second set of brain scans for each subject in the plurality of subjects generated at a second time period. In other words, each subject in the plurality of subjects has a series of scans of the subject's brain generated and stored in plurality of scans 344. The scans may be generated on a weekly basis, on a biweekly basis, on a monthly basis, every six months, or over any other cyclic period of time. In another embodiment, plurality of scans 344 includes scans generated at various irregular times. For example, the first set of scans may be taken when therapy begins, a second set of scans may be generated three months later, and a third set of scans may be generated five months later.

In this example, first set of scans 303 and second set of scans 304 are scans for subject A in plurality of scans 344. Plurality of scans 344 also includes a first set of scans and a second set of scans for every other subject in plurality of subjects 344. For example, if the plurality of subjects includes subject B and subject C, then plurality of scans 344 would include a first set of scans for subject B, a first set of scans for subject C, a second set of scans for subject B, and a second set of scans for subject C wherein the first set of scans for subject B is generated at a different time period than the second set of scans for subject B. Although FIG. 3 only shows two set of scans for subject A, any number of sets of scans may be generated. A subject may have ten sets of scans taken at different time periods, one-hundred sets of scans taken at different times, or any other number of sets of scans taken at different times.

The plurality of subjects may include subjects from various demographic groups. The various demographic groups are groups having different characteristics, such as age, age range, gender, nationality, race, pre-existing conditions, and other characteristics. Each subject in the plurality of subjects is diagnosed with a given condition in common. For example, and without limitation, all the subjects in the plurality of subjects may be diagnosed with depression. Each subject is receiving a given therapy. The given therapy may be a pharmacotherapy, a mechanical therapy, or talk therapy. In this embodiment, each subject in the plurality of subjects receives the given therapy after the first set of scans were taken at the first time and before the second set of scans were taken at the second time. However, in another embodiment, the first set of scans and the second set of scans may be taken after the given therapy is received by the subject. For example, and without limitation, a subject may have the first set of scans taken one day or one week after therapy begins and the second set of scans may be taken six months after therapy begins.

Medical data and text analytics 314 searches set of electronic medical literature sources 316 for portions of medical literature associated with the given therapy. The portions of the medical literature may include, without limitation, portions of medical literature describing the given condition, symptoms of the given condition, the given therapy, pre-existing conditions in a subject, and/or changes in regions of interest 332 occurring over time.

As described above, neuroimage analyzer 302 identifies a first set of regions of interest in the first set of brain scans for each subject in the plurality of subjects. Neuroimage analyzer 302 also identifies a second set of regions of interest in the second set of brain scans that are automatically identified for each subject. A region of interest is an area in a scan that indicates an effect of the given condition and/or an effect of the given therapy. A set of changes in the set of brain scans is identified for each subject based on a comparison of the first set of regions of interest for each subject with the second set of regions of interest for each subject. The set of changes include indicators of change occurring in corresponding regions of interest after each subject begins receiving the given therapy. An indicator may be a level of brain activity, a level of brain metabolism, a level of a brain chemical, a characteristic of a brain structure, a size of a brain structure, or any other characteristic of a feature of a region in a brain scan. For example, and without limitation, an indicator may be a size of a brain ventricle or a level of neurotransmitters in an area of the brain.

Therapy mechanism generator 348 is software for determining a drug mechanism of action based on an analysis of changes in the regions of interest for the plurality of subjects and the portions of the medical literature associated with the given condition and the given therapy. Therapy mechanism generator 348 analyzes the set of changes for each subject with the portions of the medical literature describing the given therapy to identify set of typical changes 354 attributable to the given therapy. Set of typical changes 354 are changes that occur consistently in corresponding regions of interest in a set of subjects. A change is not required to occur in the corresponding regions of interest in every subject in the plurality of subjects. The change is only required to occur in a given number of subjects to be determined to be a change that occurs consistently in corresponding regions of interest. The changes in set of typical changes 354 are changes associated with the mechanism of action of the given therapy and not changes caused by pre-existing conditions, other therapies received by one or more subjects, or any other external environmental factors.

Therapy mechanism generator 348 analyzes the portions of the medical literature with set of typical changes 354 occurring over time to derive mechanism of action 350 for the given therapy. Therapy mechanism generator 348 may also analyze additional subject data for each subject with set of typical changes 354 and the portions of the medical literature to derive mechanism of action 350. The additional subject data may include clinical data 336, subject medical history 338, behavioral data 340, and/or cognitive data 342. Therapy mechanism generator 348 may be configured to remove any changes from set of typical changes 354 that are uncorrelated with the given condition and/or the given therapy. For example, if therapy mechanism generator 348 identifies a given change as being attributable to other therapies being applied to a given subject in the plurality of subjects and/or other medical conditions in the subject, therapy mechanism generator 348 removes the given change from set of typical changes 354. Changes in the set of scans for the given subject that are attributable to the other therapies and/or the other medical conditions are identified as uncorrelated changes. All uncorrelated changes are removed from set of typical changes 354 by therapy mechanism generator 348.

Therapy mechanism generator 348 generates mechanism of action 350 based on set of typical changes 354 and quantitative information describing the given condition, the given therapy, and responses to the given therapy by subjects found in the portions of the medical literature. In one embodiment, mechanism of action 350 comprises a set of links to the portions of the medical literature associated with the given therapy and/or a set of links to each change in set of typical changes 350.

In this embodiment, neuroimage mapping manager 300 and therapy mechanism generator 348 are located on computer 301. In another embodiment, therapy mechanism generator 348 may be located on a computing device that is remote from computer 301, such as, without limitation, a remote server. In such a case, therapy mechanism generator 348 may receive changes in regions of interest 332 and/or the sets of regions of interests for each subject via a network connection to a network, such as network 102 in FIG. 1. The network may be a intranet, Ethernet, the Internet, a local area network (LAN), a wide area network (WAN), a wireless network, a private network, or any other type of network.

Figure 4:
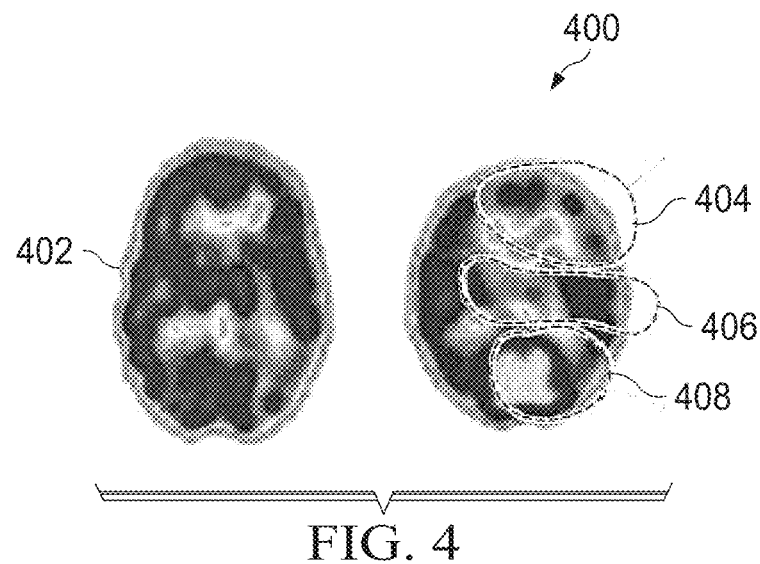
FIG. 4 is a block diagram of a magnetic resonance imaging brain scan having regions of interest in accordance with an illustrative embodiment.

Referring to FIG. 4, a block diagram of a magnetic resonance imaging brain scan having regions of interest is depicted in accordance with an illustrative embodiment. Scan 400 is a positron emission tomography scan of a brain of a subject. Scan 402 is a positron emission tomography scan of a normal, healthy subject. Scan 400 has regions of interest 404-408. Regions of interest 404-408 are areas in scan 400 that show indications of a potential condition, abnormality, chemical imbalance, illness, disease, or other deviation from an expected appearance of the scan. In this example, regions of interest 404-408 show disruptions in brain activity. Region 406 shows abnormal changes in the size of the ventricles of the brain. Region 408 shows decreased function in the frontal section.

Figure 5:
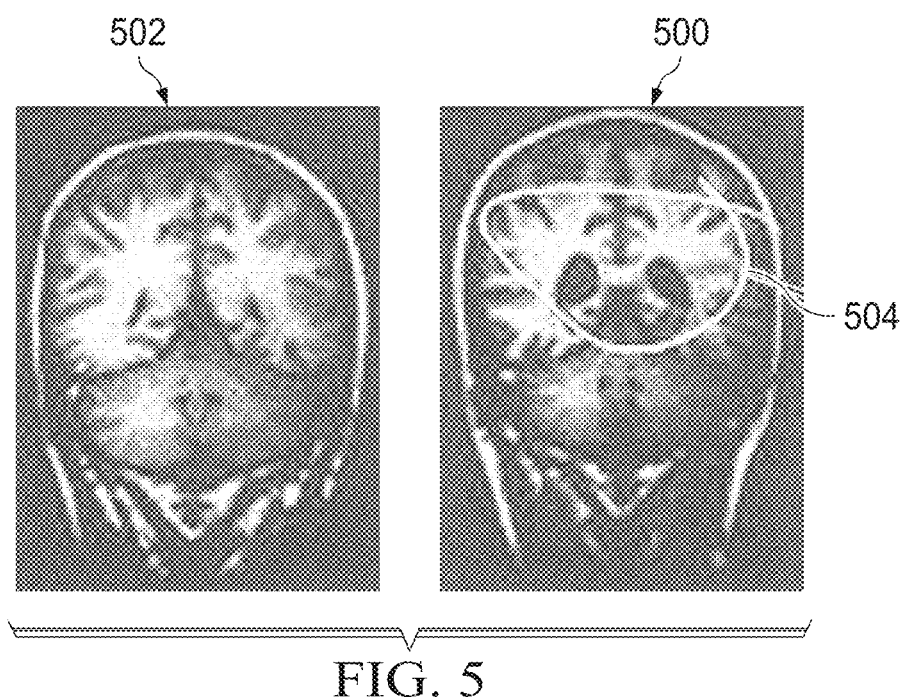
FIG. 5 is a positron emissions tomography brain scan having regions of interest in accordance with an illustrative embodiment.

Turning now to FIG. 5, a positron emissions tomography brain scan having regions of interest is shown in accordance with an illustrative embodiment. Scan 500 is a magnetic resonance imaging scan of a subject's brain. Scan 502 is a magnetic resonance imaging scan of a normal, healthy subject's brain. Scan 500 includes region of interest 504. Region 504 shows an enlargement of the ventricles of the brain when compared with scan 502 of a normal, healthy subject. The enlargement of the ventricles shown in region of interest 504 may indicate an illness or disease, such as, without limitation, schizophrenia. Therefore, a neuroimage mapping manager identifies region 504 as a region of interest.

Figure 6:
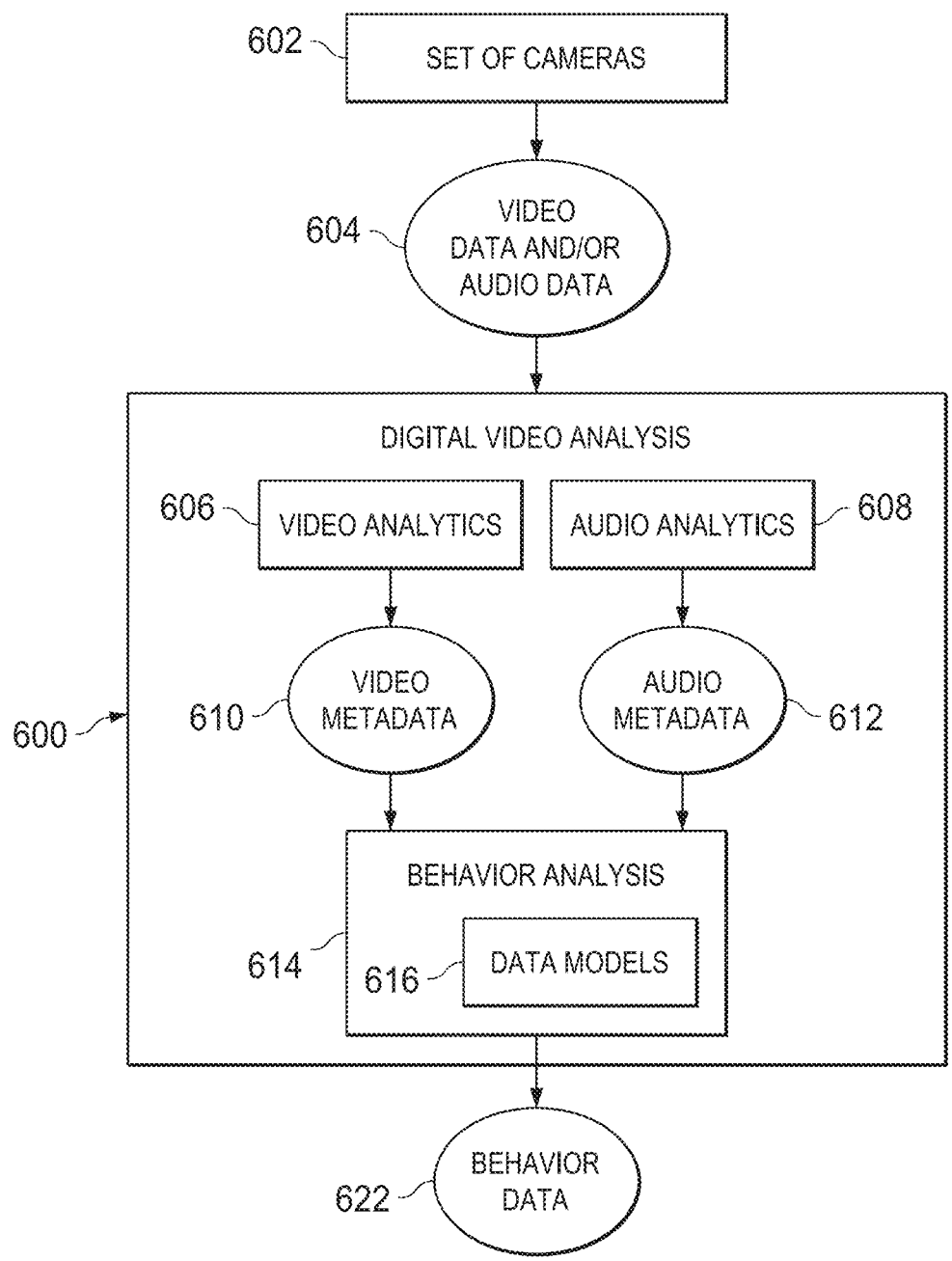
FIG. 6 is a block diagram of digital video analysis for generating behavioral data in accordance with an illustrative embodiment.

FIG. 6 is a block diagram of digital video analysis for generating behavioral data in accordance with an illustrative embodiment. Digital video analysis 600 is software for generating metadata describing the behavior of a subject by analyzing video images of the subject, such as, without limitation, International Business Machines (IBM) Smart Surveillance System (S3). Set of cameras 602 is a set of one or more cameras. Set of cameras 602 generates video data and/or audio data 604.

Digital video analysis 600 receives video data and/or audio data 604 from set of cameras 602. Video analysis 606 is a video analytics engine that automatically analyzes video images and generates video metadata 610 describing events occurring in the video data. For example, if the video data is a continuous video stream having images of subject pacing in a circle, video metadata 610 describes the speed at which the subject is pacing, the path along which the subject walks as the subject paces, and any other movements made by the subject as the subject paces.

Audio analytics 608 is an analytics engine that analyzes audio data recorded by a set of microphones and generates audio metadata 612 describing the sounds in the audio data. For example, and without limitation, audio metadata 612 may identify words spoken by the subject, the decibel level of sound, the origination point of the sound, the pitch of the sound, the type of sound, or any other description of the sound. The type of sound is an identification of what made a sound. A type of sound may be a human voice, a human cry, a sound of a footfall, tapping, humming, or any other type of sound. Behavior analysis 614 analyzes video metadata 610 and audio metadata 612 using data models 616 to identify events. The identified events are described in behavioral data 622.

Figure 7:
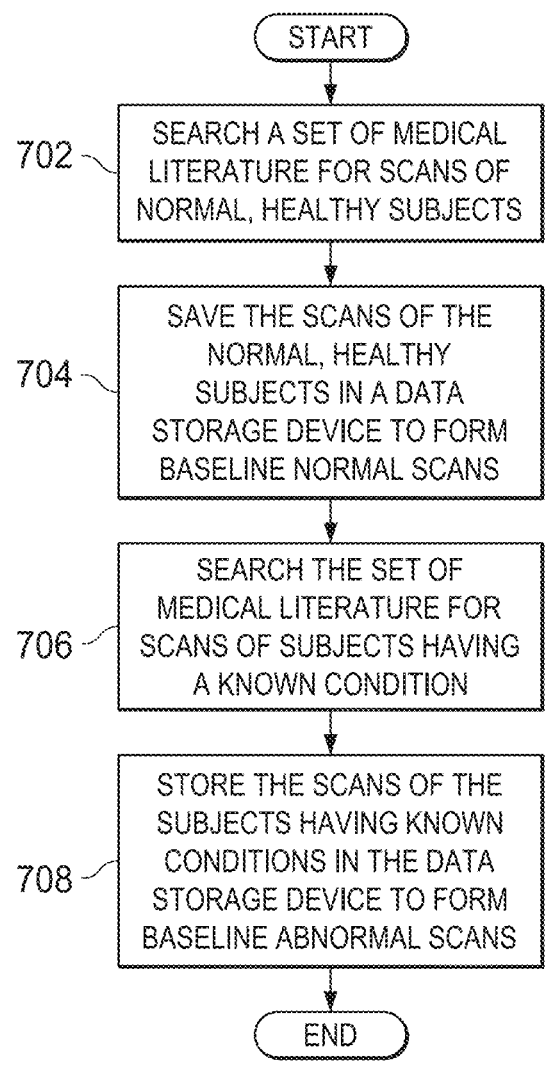
FIG. 7 is a flowchart of a process for generating baseline control scans in accordance with an illustrative embodiment.

FIG. 7 is a flowchart of a process for generating baseline control scans in accordance with an illustrative embodiment. The process in FIG. 7 may be implemented by software for generating a set of baseline control scans, such as medical data and text analytics 314 in FIGS. 3A and 3B. The baseline control scans may include baseline normal scans and/or baseline abnormal scans. Baseline normal scans are scans depicting regions of a brain that does not show indications of at least one neuropsychiatric disorder. Baseline abnormal scans are scans depicting regions of a brain that does show one or more indications of at least one neuropsychiatric disorder.

The process begins by generating baseline normal scans based on a set of scans for average healthy subjects in various demographic groups (step 702). The medical data and text analytics may obtain the set of scans for the healthy subjects by searching a set of medical literature sources for the scans of normal, healthy subjects. The scans of the normal, healthy subjects may be saved in a data storage device to form baseline normal scans.

The medical data and text analytics generates baseline abnormal scans based on a set of scans for subjects in various demographic groups diagnosed with identified conditions (step 704). The medical data and text analytics may obtain the set of scans for subjects with the identified conditions by searching the set of medical literature sources for scans of subjects having known and/or diagnosed conditions. The conditions may be a disease, an illness, an infection, a deformity, or any other condition. The scans of the subjects having the known conditions may be saved in the data storage device to form baseline abnormal scans (step 708). The medical data and text analytics generates baseline treatment scans based on a set of scans for subjects in various demographic groups diagnosed with identified conditions and undergoing identified therapies and/or treatment (step 706) with the process terminating thereafter.

Figure 8:
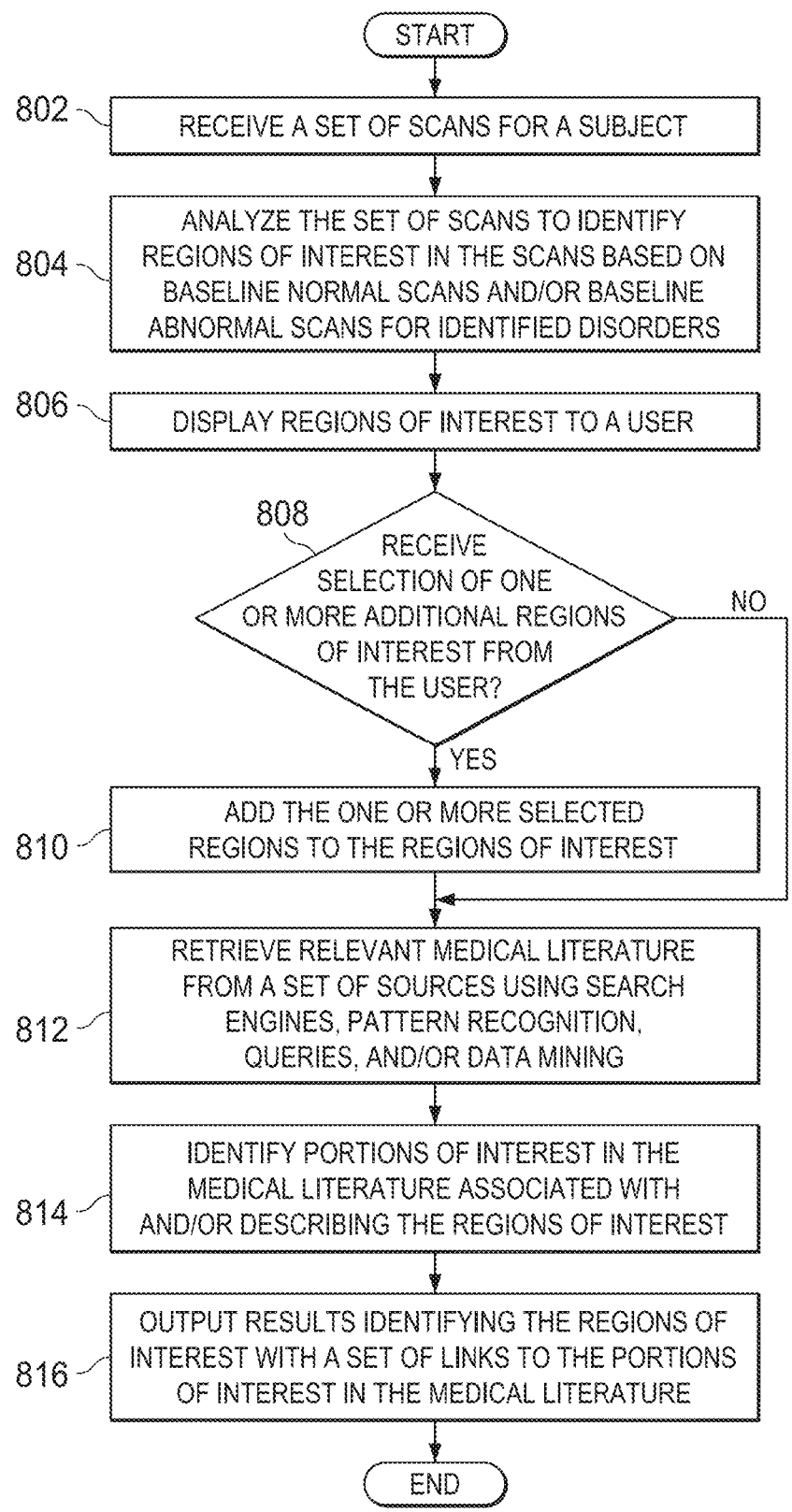
FIG. 8 is a flowchart of a process for identifying regions of interest correlated with relevant portions of the medical interest in accordance with an illustrative embodiment.

FIG. 8 is a flowchart of a process for identifying regions of interest correlated with relevant portions of the medical interest in accordance with an illustrative embodiment. The process in FIG. 8 may be implemented by software for analyzing subject brain scans to identify regions of interest in the brain scans and generate links to portions of interest in the medical literature, such as neuroimage mapping manager 300 in FIGS. 3A and 3B.

The neuroimage mapping manager receives a set of scans for a subject (step 802). The set of scans may include, without limitation, functional magnetic resonance imaging (fMRI) scans, structural magnetic resonance imaging (sMRI) scans, positron emission tomography (PET) scans, or any other type of brain scans. The neuroimage mapping manager analyzes the set of scans to identify regions of interest in the scans based on baseline normal scans and/or baseline abnormal scans for identified disorders (step 804). The neuroimage mapping manager displays the identified regions of interest to a user (step 806). The neuroimage mapping manager makes a determination as to whether a selection of one or more additional regions of interest is received from the user (step 808).

If a selection of one or more additional regions of interest is received from the user, the neuroimage mapping manager adds the one or more selected regions to the regions of interest (step 810). After adding the selected regions to the regions of interest at step 810 or if no selections of additional regions are received from the user at step 808, the neuroimage mapping manager retrieves relevant medical literature from a set of sources using search engines, pattern recognition, queries, and/or data mining (step 812). The embodiments are not limited to using only search engines, queries, and data mining. Any known or available method for locating desired information in an electronic data source may be utilized.

Next, the neuroimage mapping manager identifies portions of interest in the medical literature associated with and/or describing the regions of interest (step 814). The portions of interest may include pages, paragraphs, or portions of text describing one or more of the regions of interest, the appearance of one or more of the regions of interest, or the characteristics of one or more of the regions of interest. The portions of interest in the relevant medical literature may include images of scans containing one or more of the regions of interest, portions of text in the medical literature describing diseases, deficiencies, illnesses, and/or abnormalities that may cause the appearance of one or more of the regions of interest or one or more characteristics of the regions of interest, or any other portion of medical literature that is relevant to one or more of the regions of interest in the subject's scans. The neuroimage mapping manager outputs results identifying the regions of interest with a set of links to the portions of interest in the medical literature (step 816) with the process terminating thereafter.

In this embodiment, the regions of interest are displayed to the user and the user is given an opportunity to select one or more additional regions of interest to add to the regions of interest identified by the neuroimage mapping manager. In another embodiment, the regions of interest are not presented to the user prior to identifying the portions of interest in the medical literature. In this embodiment, the user is not required to review the regions of interest and provide input as to whether to add one or more additional regions of interest. In this case, the process may occur completely automatically without any user input during the process of analyzing the subject's scans to identify regions of interest and linking portions of the relevant medical literature to the regions of interest.

Figure 9:
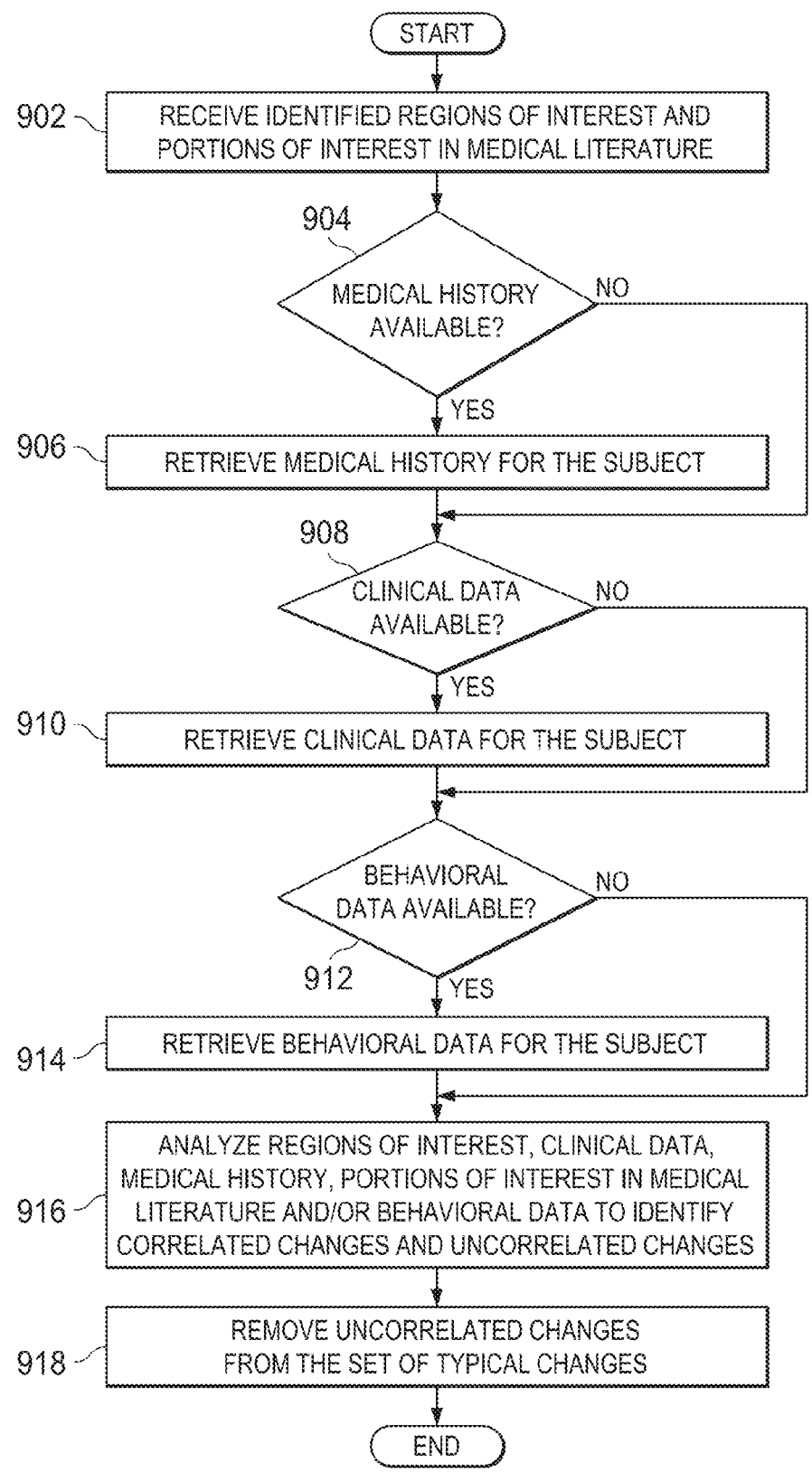
FIG. 9 is a flowchart of a process for identifying changes that are attributable to a given therapy in accordance with an illustrative embodiment.

FIG. 9 is a flowchart of a process for generating potential diagnoses for a subject based on quantitative information derived from a set of brain scans in accordance with an illustrative embodiment. The process in FIG. 9 is implemented by software for automatically generating a mechanism of action for a given therapy based on neuroimage data and portions of the medical literature, such as, without limitation, mechanism of action generator 348 in FIGS. 3A and 3B.

The process begins by receiving identified regions of interest and correlated portions of medical literature (step 902). A determination is made as to whether a medical history for the subject is available (step 904). If a medical history is available, the medical history is retrieved (step 906). After retrieving the medical history at step 906, or if the medical history is not available at step 906, a determination is made as to whether clinical data is available (step 908). If clinical data is available, the clinical data is retrieved (step 910). After retrieving the clinical data at step 910 or if clinical data is not available at step 908, a determination is made as to whether behavioral data is available (step 912). If behavioral data is available, the behavioral data is retrieved (step 914). After retrieving the behavioral data at step 914 or if behavioral data is not available, the diagnostic engine analyzes the regions of interest and portions of medical literature with any available clinical data, medical history, and/or behavioral data to identify correlated and uncorrelated changes in a set of changes occurring in a subject over time (step 916). Correlated changes are changes that are correlated with the given therapy. Uncorrelated changes are changes that are not attributable to the given therapy. Uncorrelated changes may be due to other therapies, pre-existing conditions, or other causes unrelated to the given therapy. Uncorrelated changes are removed from a set of typical changes for a particular mechanism of action (step 918) with the process terminating thereafter.

The steps shown in the flowcharts may be executed in a different order than the order shown in FIG. 9. For example, clinical data may be retrieved prior to retrieving the medical history or simultaneously with retrieving the medical history. Likewise, the behavioral data may be retrieved prior to retrieving either clinical data or medical history data. Likewise, some of the steps in FIG. 9 may be optional. For example, and without limitation, the process does not require retrieval of clinical data, retrieval of medical history data, or retrieval of behavioral data. Thus, the diagnostic engine may generate a set of potential diagnoses in step 918 without requiring an analysis of clinical data, medical history, and/or behavioral data.

Figure 10:
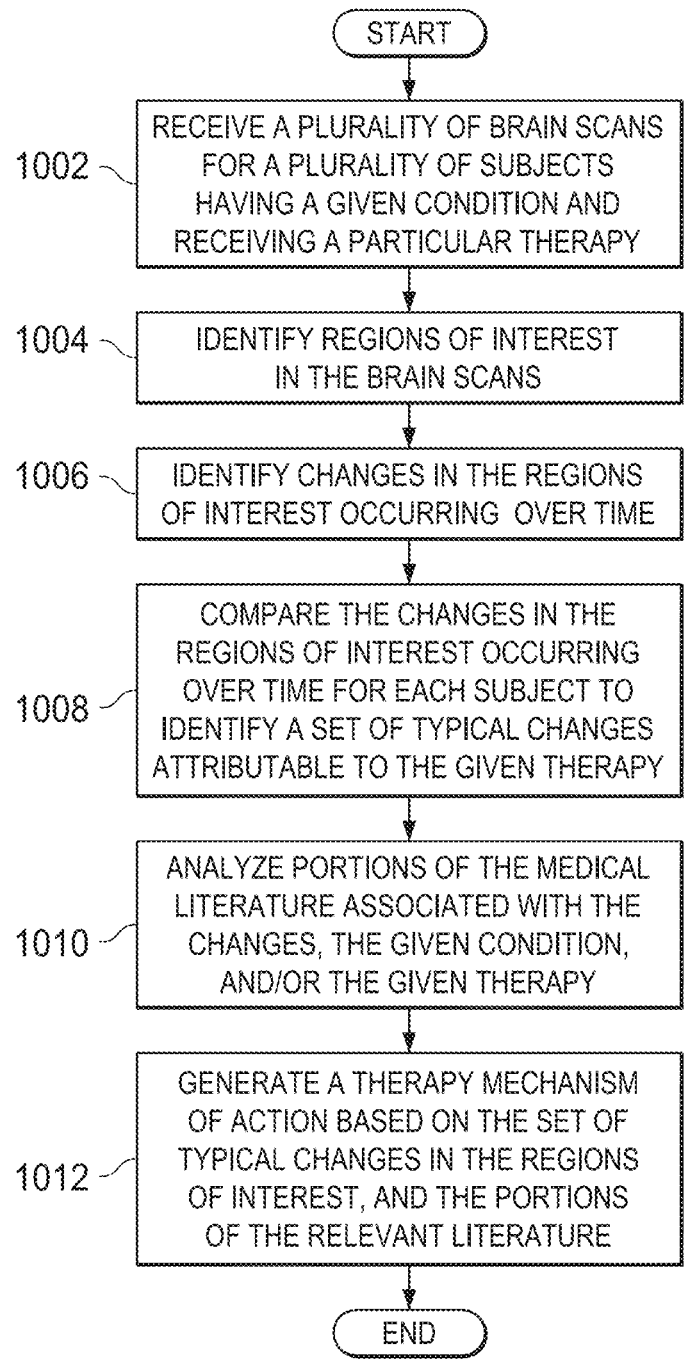
FIG. 10 is a flowchart of a process for generating a mechanism of action for a given therapy in accordance with an illustrative embodiment.

FIG. 10 is a flowchart of a process for generating a mechanism of action for a given therapy in accordance with an illustrative embodiment. The process in FIG. 10 may be implemented by software for analyzing changes in neuroimage data occurring over time and relevant portions of electronic medical literature to generate mechanisms of action for therapies, such as mechanism of action generator 348 in FIG. 3B. Steps 1004-1006 may be implemented by software for identifying regions of interest and changes in regions of interest over time, such as medical data and text analytics 314 in FIG. 3A.

The process begins by receiving a plurality of brain scans for a plurality of subjects having a given condition and receiving a particular therapy (step 1002). The process identifies regions of interest in the brain scans in the plurality of brain scans (step 1004). The process identifies changes in the regions of interest in the brain scans occurring over time (step 1006). The process compares the changes in the regions of interests occurring over time for each subject to identify a set of typical changes attributable to the given therapy (step 1008). The process analyzes portions of the medical literature associated with the given therapy, the given condition, and the set of typical changes (step 1010). The process generates the mechanism of action for the given therapy based on the analysis of the set of typical changes in the regions of interest and the portions of the medical literature (step 1012) with the process terminating thereafter.

Thus, in one embodiment, a computer implemented method, apparatus, and computer program product of determining mechanisms of action for therapies is provided. The process receives a plurality of brain scans for a plurality of subjects. The plurality of brains scans comprises a first set of brain scans for each subject in the plurality of subjects generated at a first time period and a second set of brain scans for each subject in the plurality of subjects generated at a second time period. Each subject in the plurality of subjects is diagnosed with a given condition and each subject is receiving a given therapy. The given therapy may be a pharmacotherapy, a mechanical therapy, or talk therapy.

A set of electronic medical literature sources is automatically searched for portions of medical literature describing the given therapy. A first set of regions of interest in the first set of brain scans for each subject and a second set of regions of interest in the second set of brain scans are automatically identified for each subject. A set of changes in the set of brain scans is identified for each subject based on a comparison of the first set of regions of interest for each subject with the second set of regions of interest for each subject. The set of changes is change occurring after each subject begins receiving the given therapy. The set of changes for each subject is analyzed with the portions of the medical literature describing the given therapy to identify a set of typical changes attributable to the given therapy. A mechanism of action for the given therapy is generated based on the set of typical changes.

The therapy mechanism generator automatically determines a mechanism of action of a given therapy, such as, without limitation, a drug therapy, talk therapy, or mechanical therapy, without requiring human input and human analysis of the medical literature, brain scans, and other additional subject information. The therapy mechanism generator generates mechanism of action faster and more efficiently that in the prior art. In addition, the utilization of electronic sources of relevant portions of medical literature and analysis of neuroimage data enables more accurate determination of mechanisms of action in complex cases.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method of assessing neuroimaging and medical data to determine mechanisms of action for neuropsychiatric therapies, the computer implemented method comprising:

receiving, at a processor via a network connection, neuroimaging data of a first set of human brain scans for each human subject in a plurality of human subjects diagnosed with a given neuropsychiatric condition generated at a first time period prior to beginning implementation of a neuropsychiatric therapy to treat the given neuropsychiatric condition and a second set of human brain scans for the each human subject in the plurality of human subjects diagnosed with the given neuropsychiatric condition generated at a second time period of a given amount of time after beginning the implementation of the neuropsychiatric therapy to treat the given neuropsychiatric condition, wherein a set of one or more scanning devices generate the neuroimaging data of the first set of human brain scans and the second set of human brain scans, and wherein the neuropsychiatric therapy is received by the each human subject in the plurality of human subjects diagnosed with the given neuropsychiatric condition;

automatically searching, using the processor, via the network connection a set of online electronic medical literature sources for portions of medical literature describing the neuropsychiatric therapy used to treat the given neuropsychiatric condition;

automatically identifying, using the processor, a first set of regions of interest in the first set of human brain scans for the each human subject in the plurality of human subjects diagnosed with the given neuropsychiatric condition generated at the first time period prior to beginning the implementation of the neuropsychiatric therapy to treat the given neuropsychiatric condition and a second set of regions of interest in the second set of human brain scans for the each human subject in the plurality of human subjects diagnosed with the given neuropsychiatric condition generated at the second time period of the given amount of time after beginning the implementation of the neuropsychiatric therapy to treat the given neuropsychiatric condition;

identifying, using the processor, a set of changes in the neuroimaging data of the first set of human brain scans and the second set of human brain scans for the each human subject in the plurality of human subjects diagnosed with the given neuropsychiatric condition based on a comparison of the first set of regions of interest for the each human subject with the second set of regions of interest for the each human subject, wherein the set of changes comprises indicators of change occurring after the each human subject began receiving the neuropsychiatric therapy to treat the given neuropsychiatric condition;

analyzing, using the processor, the set of changes for the each human subject with the portions of the medical literature describing the neuropsychiatric therapy used to treat the given neuropsychiatric condition to identify a set of changes attributable to the neuropsychiatric therapy;

generating, using the processor, a mechanism of action for the neuropsychiatric therapy for the plurality of human subjects diagnosed with the given neuropsychiatric condition based on the analyzing of the set of changes for the each human subject, wherein the mechanism of action comprises a set of links to the portions of the medical literature associated with the neuropsychiatric therapy and each change in the set of changes identified from an automatic searching of the set of online electronic medical literature sources;

generating, using the processor, the set of links to the portions of the medical literature associated with the neuropsychiatric therapy used to treat the given neuropsychiatric condition; and embedding, using the processor, the set of links to the portions of the medical literature associated with the neuropsychiatric therapy used to treat the given neuropsychiatric condition within the first set of regions of interest located in the first set of human brain scans for the each human subject in the plurality of human subjects diagnosed with the given neuropsychiatric condition and the second set of regions of interest located in the second set of human brain scans for the each human subject in the plurality of human subjects diagnosed with the given neuropsychiatric condition.

2. The computer implemented method of claim 1 further comprising:

analyzing additional subject data for the each human subject in the plurality of human subjects diagnosed with the given neuropsychiatric condition with the set of changes identified in the first set of human brain scans and the second set of human brain scans for the each human subject and the portions of the medical literature associated with the neuropsychiatric therapy to generate the mechanism of action for the neuropsychiatric therapy, wherein the mechanism of action comprises the set of changes identified in the first set of human brain scans and the second set of human brain scans of the plurality of human subjects and changes in clinical test results occurring over time, and wherein the additional subject data comprises at least one of clinical data, subject medical history, behavioral data, and cognitive data.

3. The computer implemented method of claim 1 further comprising:

searching the set of online electronic medical literature sources for medical literature relevant to the given neuropsychiatric condition, the neuropsychiatric therapy, and the set of changes identified in the first set of human brain scans and the second set of human brain scans for the each human subject in the plurality of human subjects diagnosed with the given neuropsychiatric condition occurring over time to form the portions of the medical literature; and analyzing the portions of the medical literature with the set of changes identified in the first set of human brain scans and the second set of human brain scans for the each human subject in the plurality of human subjects diagnosed with the given neuropsychiatric condition occurring over time to derive the mechanism of action for the neuropsychiatric therapy.

4. The computer implemented method of claim 1 wherein the plurality of human subjects comprises human subjects from various demographic groups, and wherein the each human subject in the plurality of human subjects diagnosed with the given neuropsychiatric condition receives the neuropsychiatric therapy after the first set of human brain scans were taken at the first time and before the second set of human brain scans were taken at the second time.

5. The computer implemented method of claim 1 further comprising:

receiving a set of human brain scans for a set of healthy human subjects in various demographic groups to form baseline normal human brain scans;

analyzing the baseline normal human brain scans to identify a normal appearance of areas in normal human brain scans, wherein a normal human brain scan is a scan that does not show indications of disease or abnormalities in the areas in the normal human brain scans; and comparing the set of changes identified in the first set of human brain scans and the second set of human brain scans for the each human subject in the plurality of human subjects diagnosed with the given neuropsychiatric condition with the baseline normal human brain scans to identify the mechanism of action for the neuropsychiatric therapy.

6. The computer implemented method of claim 1 wherein the first set of human brain scans and the second set of human brain scans both comprise a combination of one or more positron emission tomography scans and one or more magnetic resonance imaging scans of a human subject in the plurality of human subjects diagnosed with the given neuropsychiatric condition.

7. The computer implemented method of claim 1 further comprising:

identifying other medical conditions associated with one or more human subjects in the plurality of human subjects diagnosed with the given neuropsychiatric condition;

identifying changes in the first set of human brain scans and the second set of human brain scans for the one or more human subjects that are attributable to the other medical conditions associated with the one or more human subjects to form uncorrelated changes attributable to the other medical conditions associated with the one or more human subjects; and removing the uncorrelated changes attributable to the other medical conditions associated with the one or more human subjects from the set of changes identified in the first set of human brain scans and the second set of human brain scans for the each human subject in the plurality of human subjects diagnosed with the given neuropsychiatric condition.

8. The computer implemented method of claim 1 wherein the neuropsychiatric therapy used to treat the given neuropsychiatric condition is a pharmacotherapy, and wherein the mechanism of action for the neuropsychiatric therapy is a drug mechanism of action.

9. The computer implemented method of claim 1 wherein the neuropsychiatric therapy used to treat the given neuropsychiatric condition is selected from a group consisting of a mechanical therapy and a talk therapy.

10. A non-transitory computer readable storage medium having computer usable program code for assessing neuroimaging and medical data to determine mechanisms of action for neuropsychiatric therapies embodied therewith that is executable by a computer, the computer usable program code comprising:

computer usable program code configured to receive via a network connection neuroimaging data of a first set of human brain scans for each human subject in a plurality of human subjects diagnosed with a given neuropsychiatric condition generated at a first time period prior to beginning implementation of a neuropsychiatric therapy to treat the given neuropsychiatric condition and a second set of human brain scans for the each human subject in the plurality of human subjects diagnosed with the given neuropsychiatric condition generated at a second time period of a given amount of time after beginning the implementation of the neuropsychiatric therapy to treat the given neuropsychiatric condition, wherein a set of one or more scanning devices generate the neuroimaging data of the first set of human brain scans and the second set of human brain scans, and wherein the neuropsychiatric therapy is received by the each human subject in the plurality of human subjects diagnosed with the given neuropsychiatric condition;

computer usable program code configured to automatically search via the network connection a set of online electronic medical literature sources for portions of medical literature describing the neuropsychiatric therapy used to treat the given neuropsychiatric condition;

computer usable program code configured to automatically select a first set of regions of interest in the first set of human brain scans for the each human subject in the plurality of human subjects diagnosed with the given neuropsychiatric condition generated at the first time period prior to beginning the implementation of the neuropsychiatric therapy to treat the given neuropsychiatric condition and a second set of regions of interest in the second set of human brain scans for the each human subject in the plurality of human subjects diagnosed with the given neuropsychiatric condition generated at the second time period of the given amount of time after beginning the implementation of the neuropsychiatric therapy to treat the given neuropsychiatric condition;

computer usable program code configured to identify a set of changes in the neuroimaging data of the first set of human brain scans and the second set of human brain scans for the each human subject in the plurality of human subjects diagnosed with the given neuropsychiatric condition based on a comparison of the first set of regions of interest for the each human subject with the second set of regions of interest for the each human subject, wherein the set of changes comprises indicators of change occurring after the each human subject began receiving the neuropsychiatric therapy to treat the given neuropsychiatric condition;

computer usable program code configured to analyze the set of changes for the each human subject with the portions of the medical literature describing the neuropsychiatric therapy used to treat the given neuropsychiatric condition to identify a set of changes attributable to the neuropsychiatric therapy;

computer usable program code configured to generate a mechanism of action for the neuropsychiatric therapy for the plurality of human subjects diagnosed with the given neuropsychiatric condition based on the analyzing of the set of changes for the each human subject, wherein the mechanism of action comprises a set of links to the portions of the medical literature associated with the neuropsychiatric therapy and each change in the set of changes identified from an automatic searching of the set of online electronic medical literature sources;

computer usable program code configured to generate the set of links to the portions of the medical literature associated with the neuropsychiatric therapy used to treat the given neuropsychiatric condition; and computer usable program code configured to embed the set of links to the portions of the medical literature associated with the neuropsychiatric therapy used to treat the given neuropsychiatric condition within the first set of regions of interest located in the first set of human brain scans for the each human subject in the plurality of human subjects diagnosed with the given neuropsychiatric condition and the second set of regions of interest located in the second set of human brain scans for the each human subject in the plurality of human subjects diagnosed with the given neuropsychiatric condition.

11. The non-transitory computer readable storage medium of claim 10 wherein the computer usable program code further comprises:

computer usable program code configured to analyze additional subject data for the each human subject in the plurality of human subjects diagnosed with the given neuropsychiatric condition with the set of changes identified in the first set of human brain scans and the second set of human brain scans for the each human subject and the portions of the medical literature associated with the neuropsychiatric therapy to generate the mechanism of action for the neuropsychiatric therapy, wherein the mechanism of action comprises the set of changes identified in the first set of human brain scans and the second set of human brain scans of the plurality of human subjects and changes in clinical test results occurring over time, and wherein the additional subject data comprises at least one of clinical data, subject medical history, behavioral data, and cognitive data.

12. The non-transitory computer readable storage medium of claim 10 wherein the computer usable program code further comprises:

computer usable program code configured to search the set of online electronic medical literature sources for medical literature relevant to the given neuropsychiatric condition, the neuropsychiatric therapy, and the set of changes identified in the first set of human brain scans and the second set of human brain scans for the each human subject in the plurality of human subjects diagnosed with the given neuropsychiatric condition occurring over time to form the portions of the medical literature; and computer usable program code configured to analyze the portions of the medical literature with the set of changes identified in the first set of human brain scans and the second set of human brain scans for the each human subject in the plurality of human subjects diagnosed with the given neuropsychiatric condition occurring over time to derive the mechanism of action for the neuropsychiatric therapy.

13. The non-transitory computer readable storage medium of claim 10 wherein the plurality of human subjects comprises human subjects from various demographic groups, and wherein the each human subject in the plurality of human subjects diagnosed with the given neuropsychiatric condition receives the neuropsychiatric therapy after the first set of human brain scans were taken at the first time and before the second set of human brain scans were taken at the second time.

14. The non-transitory computer readable storage medium of claim 10 wherein the computer usable program code further comprises:
computer usable program code configured to receive a set of human brain scans for a set of healthy human subjects in various demographic groups to form baseline normal human brain scans;
computer usable program code configured to analyze the baseline normal human brain scans to identify a normal appearance of areas in normal human brain scans, wherein a normal human brain scan is a scan that does not show indications of disease or abnormalities in the areas in the normal human brain scans; and
computer usable program code configured to compare the set of changes identified in the first set of human brain scans and the second set of human brain scans for the each human subject in the plurality of human subjects diagnosed with the given neuropsychiatric condition with the baseline normal human brain scans to identify the mechanism of action for the neuropsychiatric therapy.

15. The non-transitory computer readable storage medium of claim 10 wherein the computer usable program code further comprises:
computer usable program code configured to identify other medical conditions associated with one or more human subjects in the plurality of human subjects diagnosed with the given neuropsychiatric condition;
computer usable program code configured to identify changes in the first set of human brain scans and the second set of human brain scans for the one or more human subjects that are attributable to the other medical conditions associated with the one or more human subjects to form uncorrelated changes attributable to the other medical conditions associated with the one or more human subjects; and
computer usable program code configured to remove the uncorrelated changes attributable to the other medical conditions associated with the one or more human subjects from the set of changes identified in the first set of human brain scans and the second set of human brain scans for the each human subject in the plurality of human subjects diagnosed with the given neuropsychiatric condition.

16. The non-transitory computer readable storage medium of claim 10 wherein the neuropsychiatric therapy used to treat the given neuropsychiatric condition is selected from a group consisting of a pharmacotherapy, a mechanical therapy, and a talk therapy.

17. An apparatus for assessing neuroimaging and medical data to determine mechanisms of action for neuropsychiatric therapies comprising:
a bus system;
a communications system coupled to the bus system;
a non-transitory computer readable storage medium connected to the bus system, wherein the non-transitory computer readable storage medium stores computer usable program code; and
a processor chip coupled to the bus system, wherein the processor chip executes the computer usable program code to:
receive via a network connection neuroimaging data of a first set of human brain scans for each human subject in a plurality of human subjects diagnosed with a given neuropsychiatric condition generated at a first time period prior to beginning implementation of a neuropsychiatric therapy to treat the given neuropsychiatric condition and a second set of human brain scans for the each human subject in the plurality of human subjects diagnosed with the given neuropsychiatric condition generated at a second time period of a given amount of time after beginning the implementation of the neuropsychiatric therapy to treat the given neuropsychiatric condition, wherein a set of one or more scanning devices generate the neuroimaging data of the first set of human brain scans and the second set of human brain scans, and wherein the neuropsychiatric therapy is received by the each human subject in the plurality of human subjects diagnosed with the given neuropsychiatric condition;
automatically search via the network connection a set of online electronic medical literature sources for portions of medical literature describing the neuropsychiatric therapy used to treat the given neuropsychiatric condition;
analyze the first set of brain scans and the second set of brain scans to identify a first set of regions of interest in the first set of human brain scans for the each human subject in the plurality of human subjects diagnosed with the given neuropsychiatric condition generated at the first time period prior to beginning the implementation of the neuropsychiatric therapy to treat the given neuropsychiatric condition and a second set of regions of interest in the second set of human brain scans for the each human subject in the plurality of human subjects diagnosed with the given neuropsychiatric condition generated at the second time period of the given amount of time after beginning the implementation of the neuropsychiatric therapy to treat the given neuropsychiatric condition;
identify a set of changes in the neuroimaging data of the first set of human brain scans and the second set of human brain scans for the each human subject in the plurality of human subjects diagnosed with the given neuropsychiatric condition based on a comparison of the first set of regions of interest for the each human subject with the second set of regions of interest for the each human subject, wherein the set of changes comprises indicators of change occurring after the each human subject began receiving the neuropsychiatric therapy to treat the given neuropsychiatric condition;
analyze the set of changes for the each human subject with the portions of the medical literature describing the neuropsychiatric therapy used to treat the given neuropsychiatric condition to identify a set of changes attributable to the neuropsychiatric therapy;
generate the set of links to the portions of the medical literature associated with the neuropsychiatric therapy used to treat the given neuropsychiatric condition; and
embed the set of links to the portions of the medical literature associated with the neuropsychiatric therapy used to treat the given neuropsychiatric condition within the first set of regions of interest located in the first set of human brain scans for the each human subject in the plurality of human subjects diagnosed with the given neuropsychiatric condition and the second set of regions of interest located in the second set of human brain scans for the each human subject in the plurality of human subjects diagnosed with the given neuropsychiatric condition.

18. The apparatus of claim 17 wherein the processor chip further executes the computer usable program code to analyze additional subject data for the each human subject in the plurality of human subjects diagnosed with the given neuropsychiatric condition with the set of changes identified in the first set of human brain scans and the second set of human brain scans for the each human subject and the portions of the medical literature associated with the neuropsychiatric therapy to generate the mechanism of action for the neuropsychiatric therapy, wherein the mechanism of action comprises the set of changes identified in the first set of human brain scans and the second set of human brain scans of the plurality of human subjects and changes in clinical test results occurring over time, and wherein the additional subject data comprises at least one of clinical data, subject medical history, behavioral data, and cognitive data.

19. The apparatus of claim 17 wherein the processor chip further executes the computer usable program code to identify other medical conditions associated with one or more human subjects in the plurality of human subjects diagnosed with the given neuropsychiatric condition; identify changes in the first set of human brain scans and the second set of human brain scans for the one or more human subjects that are attributable to the other medical conditions associated with the one or more human subjects to form uncorrelated changes attributable to the other medical conditions associated with the one or more human subjects; and remove the uncorrelated changes attributable to the other medical conditions associated with the one or more human subjects from the set of changes identified in the first set of human brain scans and the second set of human brain scans for the each human subject in the plurality of human subjects diagnosed with the given neuropsychiatric condition.

20. A data processing system for assessing neuroimaging and medical data to determine mechanisms of action for neuropsychiatric therapies comprising:
a set of online electronic medical literature sources, wherein the set of online medical literature sources comprises medical literature;
a neuroimage mapping manager, wherein the neuroimage mapping manager automatically retrieves via a network connection portions of the medical literature that describe a neuropsychiatric therapy from the set of online electronic medical literature sources; analyzes neuroimaging data corresponding to a plurality of human brain scans for a plurality of human subjects diagnosed with a given neuropsychiatric condition who receive the neuropsychiatric therapy to identify a first set of regions of interest in a first set of human brain scans for each human subject in the plurality of human subjects diagnosed with the given neuropsychiatric condition and a second set of regions of interest in a second set of human brain scans for each human subject in the plurality of human subjects diagnosed with the given neuropsychiatric condition and identifies a set of changes in the neuroimaging data of the first set of human brain scans and the second set of human brain scans for each human subject in the plurality of human subjects diagnosed with the given neuropsychiatric condition based on a comparison of the first set of regions of interest for each human subject with the second set of regions of interest for each human subject, wherein the first set of brain scans for each human subject in the plurality of human subjects diagnosed with the given neuropsychiatric condition is generated at a first time period prior to beginning implementation of the neuropsychiatric therapy to treat the given neuropsychiatric condition and the second set of human brain scans for each human subject in the plurality of human subjects diagnosed with the given neuropsychiatric condition is generated at a second time period of a given amount of time after beginning the implementation of the neuropsychiatric therapy to treat the given neuropsychiatric condition, and wherein a set of one or more scanning devices generate the neuroimaging data of the first set of human brain scans and the second set of human brain scans, and wherein the neuropsychiatric therapy is administered to each human subject in the plurality of human subjects diagnosed with the given neuropsychiatric condition, and wherein the set of changes identified in the first set of human brain scans and the second set of human brain scans for each human subject in the plurality of human subjects diagnosed with the given neuropsychiatric condition is changes that occur after each human subject began to receive the neuropsychiatric therapy; and
a therapy mechanism generator, wherein the therapy mechanism generator analyzes the set of changes for each human subject with the portions of the medical literature that describe the neuropsychiatric therapy used to treat the given neuropsychiatric condition to identify a set of changes attributable to the neuropsychiatric therapy; generates a mechanism of action for the neuropsychiatric therapy based on the set of changes, wherein the mechanism of action comprises a set of links to the portions of the medical literature associated with the neuropsychiatric therapy and each change in the set of changes identified from an automatic searching of the set of online electronic medical literature sources; generates the set of links to the portions of the medical literature associated with the neuropsychiatric therapy used to treat the given neuropsychiatric condition; and embeds the set of links to the portions of the medical literature associated with the neuropsychiatric therapy used to treat the given neuropsychiatric condition within the first set of regions of interest located in the first set of human brain scans for the each human subject in the plurality of human subjects diagnosed with the given neuropsychiatric condition and the second set of regions of interest located in the second set of human brain scans for the each human subject in the plurality of human subjects diagnosed with the given neuropsychiatric condition.

21. The data processing system of claim 20 further comprising:
a data storage device, wherein the data storage device stores additional subject data for each human subject in the plurality of human subjects diagnosed with the given neuropsychiatric condition, and wherein the therapy mechanism generator analyzes the additional subject data for each human subject with the set of changes and portions of the medical literature associated with the neuropsychiatric therapy to generate the mechanism of action for the neuropsychiatric therapy, and wherein the mechanism of action for the neuropsychiatric therapy comprises the set of changes identified in the first set of human brain scans and the second set of human brain scans of the plurality of human subjects diagnosed with the given neuropsychiatric condition and changes in clinical test results occurring over time, and wherein the additional subject data comprises at least one of clinical data, subject medical history, behavioral data, and cognitive data.

22. The data processing system of claim 20 wherein the neuropsychiatric therapy used to treat the given neuropsychiatric condition is a pharmacotherapy, and wherein the mechanism of action for the neuropsychiatric therapy is a drug mechanism of action.

\* \* \* \* \*